(12) United States Patent
Johnson et al.

(10) Patent No.: US 8,093,453 B2
(45) Date of Patent: Jan. 10, 2012

(54) CORN EVENT 3272 AND METHODS OF DETECTION THEREOF

(75) Inventors: Brian Johnson, Research Triangle Park, NC (US); Tanya Markham, Durham, NC (US); Vladimir Samoylov, Chapel Hill, NC (US); Kenneth Dallmier, Bloomington, IL (US)

(73) Assignee: Syngenta Participations AG, Basel (CH)

( * ) Notice: Subject to any disclaimer, the term of this patent is extended or adjusted under 35 U.S.C. 154(b) by 194 days.

(21) Appl. No.: 12/608,017

(22) Filed: Oct. 29, 2009

(65) Prior Publication Data

US 2010/0063265 A1  Mar. 11, 2010

Related U.S. Application Data

(62) Division of application No. 11/370,799, filed on Mar. 8, 2006, now Pat. No. 7,635,799.

(51) Int. Cl.
*A01H 5/00* (2006.01)
*A01H 4/00* (2006.01)
*C12N 15/00* (2006.01)
*C12N 15/05* (2006.01)

(52) U.S. Cl. ..... 800/278; 800/284; 800/295; 800/320.1; 435/410; 435/412

(58) Field of Classification Search .................. None
See application file for complete search history.

(56) References Cited

U.S. PATENT DOCUMENTS

| | | | |
|---|---|---|---|
| 5,366,883 A | 11/1994 | Asada | |
| 5,705,375 A | 1/1998 | VanOoyen et al. | |
| 5,981,835 A | 11/1999 | Austin-Phillips et al. | |
| 6,147,277 A | 11/2000 | Gausing et al. | |
| 6,737,563 B2 | 5/2004 | Yu et al. | |
| 2003/0125534 A1 | 7/2003 | Callen et al. | |
| 2003/0135885 A1 | 7/2003 | Lanahan et al. | |
| 2003/0145347 A1 | 7/2003 | Lanahan et al. | |
| 2004/0018607 A1 | 1/2004 | Callen et al. | |
| 2004/0058052 A1* | 3/2004 | Ulrich et al. | 426/629 |
| 2005/0235382 A1* | 10/2005 | Ahrens et al. | 800/289 |

FOREIGN PATENT DOCUMENTS

| | | |
|---|---|---|
| WO | WO92/05259 | 4/1992 |
| WO | WO97/32986 | 9/1997 |
| WO | WO98/39461 | 9/1998 |
| WO | WO03/018766 | 3/2003 |
| WO | WO2005/096804 | 10/2005 |

OTHER PUBLICATIONS

Dong et al., "Cloning, Sequencing, and Expression of the Gene Encoding Extracellular α-Amylase from Pyrococcus Furiosus and Biochemical Characterization of the Recombinant Enzyme", Applied and Environmental Microbiology, (Sep. 1997) pp. 3569-3576.
Syngenta Participations AG, "International Application Ser. No. PCT/US06/08090", International Search Report, (Jul. 15, 2008).
Syngenta Participations AG, "International Application Ser. No. PCT/US06/08090", Written Opinion, (Jul. 15, 2008).
GenBank Accession No. AF504062 [online], [retrieved on May 2, 2007]. Retrieved from the Internet: <URL: http://www.ncbi.nlm.nih.gov>, 2002.
GenBank Accession No. AF068255 [online], [retrieved on May 2, 2007]. Retrieved from the Internet: <URL: http://www.ncbi.nlm.nih.gov>, 2000.
Database EMBL [Online] "PUBEY88TD ZM_0.6_1.0_KB Zea mays genomic clone ZMMBTa040007, DNA sequence" XP002544125 (Feb. 6, 2003).
Database EMBL [Online] "Chlamydomonas reinhardtii cDNA clone:HC008g12_r, 5' end." XP002544123 (Oct. 4, 2000).
Database EMBL [Online] "Tetraodon nigroviridis genome survey sequence PUC-Ori end of clone 132H18 of library G from Tetraodon nigroviridis" XP002544124 (May 13, 2000).
Syngenta Participations AG, "EP Application No. 06737280.5", Extended European Search Report, (Sep. 16, 2009).

* cited by examiner

*Primary Examiner* — Brent T Page
(74) *Attorney, Agent, or Firm* — Joshua L. Price

(57) ABSTRACT

A novel transgenic corn event designated 3272, is disclosed. The invention relates to DNA sequences of the recombinant constructs inserted into the corn genome that resulted in the 3272 event and of genomic sequences flanking the insertion sites as well as to assays for detecting the presence of the 3272 event based on these novel sequences. The invention further relates to seeds of corn plants comprising the 3272 genotype, to corn plants comprising the genotype of 3272 and to methods for producing a corn plant by crossing a corn plant comprising the 3272 genotype with itself or another corn variety.

7 Claims, No Drawings

CORN EVENT 3272 AND METHODS OF DETECTION THEREOF

RELATED APPLICATIONS

This application is a divisional of U.S. patent application Ser. No. 11/370,799 filed Mar. 8, 2006, currently pending, which claims benefit of U.S. Provisional Patent Application Ser. No. 60/662,410 filed Mar. 16, 2005 and U.S. Provisional Patent Application Ser. No. 60/773,847 filed Feb. 16, 2006.

FIELD OF THE INVENTION

The present invention relates generally to the field of plant molecular biology, plant transformation, and plant breeding. More specifically, the invention relates to self-processing transgenic corn plants comprising a novel transgenic genotype and to methods of detecting the presence of the corn plant DNA in a sample and compositions thereof.

BACKGROUND

Enzymes are used to process a variety of agricultural products such as wood, fruits and vegetables, starches, juices, and the like. Typically, processing enzymes are produced and recovered on an industrial scale from various sources, such as microbial fermentation (*Bacillus* α-amylase), or isolation from plants (coffee β-galactosidase or papain from plant parts). Enzyme preparations are used in different processing applications by mixing the enzyme and the substrate under the appropriate conditions of moisture, temperature, time, and mechanical mixing such that the enzymatic reaction is achieved in a commercially viable manner. One area where enzymes play an important role is in the area of corn milling.

Today corn is milled to obtain cornstarch and other corn-milling co-products such as corn gluten feed, corn gluten meal, and corn oil. The starch obtained from the process is often further processed into other products such as derivatized starches and sugars, or fermented to make a variety of products including alcohols or lactic acid.

The process of starch recovery from corn grain is well known and involves a wet-milling process. Corn wet-milling involves many time consuming and costly steps, which include steeping the corn kernel, grinding the corn kernel and separating the components of the kernel. Dry-mill processes of making fermentable sugars (and then ethanol, for example) from cornstarch facilitate efficient contacting of exogenous enzymes with starch. These processes are less capital intensive than wet-milling but significant cost advantages are still desirable, as often the co-products derived from these processes are not as valuable as those derived from wet-milling.

Thus, for dry milling, there is a need for a method that improves the efficiency of the process and/or increases the value of the co-products. For wet milling, there is a need for a method of processing starch that does not require the equipment necessary for prolonged steeping, grinding, milling, and/or separating the components of the kernel. For example, there is a need to modify or eliminate the steeping step in wet milling as this would reduce the amount of waste water requiring disposal, thereby saving energy and time, and increasing mill capacity (kernels would spend less time in steep tanks). There is also a need to eliminate or improve the process of separating the starch-containing endosperm from the embryo.

The present invention relates to a self-processing transgenic corn (*Zea mays*) plant that has incorporated into its genome a synthetic α-amylase gene (amy797E), encoding a thermostable Amy797E α-amylase capable of processing starch in plants. Upon expression and activation of the α-amylase, the plant or plant part processes the substrate upon which the α-amylase acts. This "self-processing" results in significant improvement in making starch available for fermentation. Thus, methods which employ such plants and plant parts can eliminate the need to mill or otherwise physically disrupt the integrity of plant parts prior to recovery of starch-derived products. The transgenic corn event also has incorporated in its genome a manA gene, hereinafter called the pmi gene, encoding a phosphomannose isomerase enzyme (PMI), useful as a selectable marker, which allows the plant to utilize mannose as a carbon source.

The expression of foreign genes in plants can to be influenced by their location in the plant genome, perhaps due to chromatin structure or the proximity of transcriptional regulatory elements close to the integration site (Weising et al., 1988, Ann Rev. Genet. 22:421-477). For this reason, it is often necessary to screen a large number of events in order to identify an event characterized by optimal expression of an introduced gene of interest. For example, it has been observed in plants and in other organisms that there may be wide variations in levels of expression of a heterologous gene introduced into the chromosome of a plant's genome among individually selected events. There may also be differences in spatial or temporal patterns of expression, for example, differences in the relative expression of a transgene in various plant tissues, that may not correspond to the patterns expected from transcriptional regulatory elements present in the introduced gene construct. Therefore, it is common to produce hundreds of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, such as promoters, terminators, marker genes, and the like, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same or similar DNA construct unless the sequence of the flanking DNA adjacent to the inserted heterologous DNA is known.

SUMMARY

The present invention is drawn to a transgenic corn event, designated 3272, comprising a novel transgenic genotype that comprises a amy797E α-amylase gene and a pmi gene which confers on the plant the ability to hydrolyze starch under high temperatures and the ability to utilize mannose as a carbon source, respectively, to the 3272 corn event and progeny thereof. The present invention also provides compositions and methods for detecting the presence of nucleic acids from event 3272 based on the DNA sequence of the recombinant expression cassettes inserted into the corn genome that resulted in the 3272 event and of genomic sequences flanking the insertion site. The invention also provides transgenic corn plants comprising the genotype of the invention, seed from transgenic corn plants comprising the genotype of the invention, and to methods for producing a transgenic corn plant comprising the genotype of the invention by crossing a corn inbred comprising the genotype of the invention with itself or another corn line of a different genotype. The transgenic corn plants of the invention may have essentially all of the morphological and physiological characteristics of the corresponding isogenic non-transgenic corn plant in addition to those conferred upon the corn plant by the novel genotype of the invention. The 3272 event can be further characterized by analyzing expression levels of the Amy797E and PMI proteins as well as by testing the enzyme activity of the plants.

According to one aspect, the present invention provides an isolated nucleic acid molecule comprising at least 10 contiguous nucleotides of a heterologous DNA sequence inserted into the corn plant genome of corn event 3272 and at least 10 contiguous nucleotides of a corn plant genome DNA flanking the point of insertion of a heterologous DNA sequence inserted into the corn plant genome of corn event 3272. The isolated nucleic acid molecule according to this aspect may comprise at least 20 or at least 50 contiguous nucleotides of a heterologous DNA sequence inserted into the corn plant genome of corn event 3272 and at least 20 or at least 50 contiguous nucleotides of a corn plant genome DNA flanking the point of insertion of a heterologous DNA sequence inserted into the corn plant genome of corn event 3272.

According to another aspect, the present invention provides an isolated nucleic acid molecule comprising a nucleotide sequence that comprises at least one junction sequence of event 3272 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the 3272 event.

According to another aspect, the present invention provides an isolated nucleic acid linking a heterologous DNA molecule to the corn plant genome in corn event 3272 comprising a sequence of from about 11 to about 20 contiguous nucleotides selected from the group consisting of SEQ ID NO: 1, SEQ ID NO: 2, and complements thereof.

According to another aspect, the present invention provides an isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting event 3272 are provided. Such flanking sequence primers comprise an isolated nucleotide sequence of at least 10-15 contiguous nucleotides from nucleotides 1-1409 of SEQ ID NO: 3 (arbitrarily designated herein as the 5' flanking sequence), or the complements thereof. In one embodiment of this aspect the flanking sequence primers are selected from the group consisting of SEQ ID NO: 34, SEQ ID NO: 35, SEQ ID NO: 39, SEQ ID NO: 45, and SEQ ID NO: 48, and the complements thereof.

In another aspect of the invention, the flanking sequence primers comprise a nucleotide sequence of at least 10-15 contiguous nucleotides from nucleotides 322-1879 of SEQ ID NO: 4 (arbitrarily designated herein as the 3' flanking sequence), or the complements thereof. In one embodiment of this aspect the flanking sequence primers are selected from the group consisting of SEQ ID NO: 36 and SEQ ID NO: 42, and the complements thereof According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 3, or SEQ ID NO: 4) and a second primer comprising a nucleotide sequence of at least 10-15 contiguous nucleotides of heterologous DNA inserted into the event 3272 genome. The second primer preferably comprises a nucleotide sequence which is or is complementary to the insert sequence adjacent to the plant genomic flanking DNA sequence as set forth in SEQ ID NO: 3 from nucleotide position 1410 through 1600 and in SEQ ID NO: 4 from nucleotide position 1 through 321.

According to another aspect of the invention, methods of detecting the presence of DNA corresponding to event 3272 in a biological sample are provided. Such methods comprise: (a) contacting the sample comprising DNA with a pair of primers that, when used in a nucleic-acid amplification reaction with genomic DNA from corn event 3272; produces an amplicon that is diagnostic for corn event 3272; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, SEQ ID NO: 4, and compliments thereof.

According to another aspect, the invention provides methods of detecting the presence of a DNA corresponding to the 3272 event in a biological sample. Such methods comprise: (a) contacting the sample comprising DNA with a probe that hybridizes under high stringency conditions with genomic DNA from corn event 3272 and does not hybridize under high stringency conditions with DNA of a control corn plant; (b) subjecting the sample and probe to high stringency hybridization conditions; and (c) detecting hybridization of the probe to the DNA.

According to another aspect of the invention, a kit is provided for the detection of event 3272 nucleic acids in a biological sample. The kit includes at least one DNA sequence comprising a sufficient length of polynucleotides which is or is complementary to SEQ ID NO: 1, SEQ ID NO: 2, SEQ ID NO: 3, or SEQ ID NO: 4, wherein the DNA sequences are useful as primers or probes that hybridize to isolated DNA from event 3272, and which, upon amplification of or hybridization to a nucleic acid sequence in a sample followed by detection of the amplicon or hybridization to the target sequence, are diagnostic for the presence of nucleic acid sequences from event 3272 in the sample. The kit further includes other materials necessary to enable nucleic acid hybridization or amplification methods.

In another aspect, the present invention provides a method of detecting corn event 3272 protein in a biological sample comprising: (a) extracting protein from a sample of corn event 3272 tissue; (b) assaying the extracted protein using an immunological method comprising antibody specific for the insecticidal or selectable marker protein produced by the 3272 event; and (c) detecting the binding of said antibody to the insecticidal or selectable marker protein.

In another aspect, the present invention provides a biological sample derived from a event 3272 corn plant, tissue, or seed, wherein the sample comprises a nucleotide sequence which is or is complementary to a sequence selected from the group consisting of SEQ ID NO: 1, and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the present invention provides an extract derived from a event 3272 corn plant, tissue, or seed comprising a nucleotide sequence which is or is complementary to a nucleotide sequence selected from the group consisting of SEQ ID NO: 1, and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided.

According to another aspect, the present invention provides a method for producing a corn plant resistant to at least corn rootworm infestation comprising: (a) sexually crossing a first parent corn plant with a second parent corn plant, wherein said first or second parent corn plant comprises corn event 3272 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that is at least resistant to corn rootworm infestation; wherein the second generation progeny plants comprise a nucleotide sequence selected from the group consisting of SEQ ID NO: 1 and SEQ ID NO: 2.

According to yet another aspect, the present invention provides a method for producing corn seed comprising crossing a first parent corn plant with a second parent corn plant and harvesting the resultant first generation corn seed, wherein the first or second parent corn plant is an inbred corn plant of the invention.

According to another aspect, the present invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

The foregoing and other aspects of the invention will become more apparent from the following detailed description.

Deposits

Seeds for event 3272 have been deposited in accordance with Budapest Treaty Rule 7.3 and Rule 10.2 and received by the American Type Culture Collection (ATCC®), (10801 University Boulevard Manassas, Va. 20110-2209 USA Telephone: (800) 638-6597), on Apr. 22, 2009 and given ATCC® Patent Deposit Designation PTA-9972.

Description of the Sequences in the Sequence Listing

SEQ ID NO: 1 is the 5' genome-insert junction.
SEQ ID NO: 2 is the 3' insert-genome junction.
SEQ ID NO: 3 is the 5' genome+insert sequence.
SEQ ID NO: 4 is the 3' insert+genome sequence.
SEQ ID NO: 5 is corn genome flanking 5' to insert.
SEQ ID NO: 6 is corn genome flanking 3' to insert.
SEQ ID Nos: 7-9 are amy797E primers and probe.
SEQ ID Nos: 10-12 are pmi primers and probe.
SEQ ID NO: 13-15 are ZmAdh1 primers and probe.
SEQ ID Nos: 16-27 are insert DNA specific primers.
SEQ ID NO: 28-31 are degenerate TAIL PCR primers.
SEQ ID NO: 32 is an outer GenomeWalker® primer.
SEQ ID NO: 33 is a nested adapter primer.
SEQ ID NO: 34-35 are 5' flanking sequence primers.
SEQ ID NO: 36 is a 3' flanking sequence primer.
SEQ ID NO: 37 is the sequence of the heterologous DNA inserted in to 3272.
SEQ ID NO: 38 is the ER retention signal sequence.
SEQ ID NO: 39 is the AmyF1n-5' primer.
SEQ ID NO: 40 is the AmyF1n-3' primer.
SEQ ID NO: 41 is the AmyF2-5' primer.
SEQ ID NO: 42 is the AmyF2-3' primer.
SEQ ID NO: 43 is the F1 amplicon.
SEQ ID NO: 44 is the F2 amplicon.
SEQ ID NO: 45 is the Es3272-5' forward primer.
SEQ ID NO: 46 is the Es3272-5' reverse primer.
SEQ ID NO: 47 is the Es3272-5' probe.
SEQ ID NO: 48 is the ESPCR0026 primer.
SEQ ID NO: 49 is the ESPCR0004 primer.
SEQ ID NO: 50-52 are ZmAdh1 primers and probe.

Definitions

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in, for example, Rieger et al., Glossary of Genetics: Classical and Molecular, 5$^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein the term "amy797E gene" refers to a coding sequence that encodes the thermostable 797GL3 α-amylase (Lanahan et al., US Patent Application Publication No. 20030135885, published Jul. 17, 2003) fused to a 19 amino acid N-terminal maize γ-zein signal sequence and a C-terminal SEKDEL (SEQ ID NO: 38) endoplasmic reticulum retention signal (ER rs).

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Detection kit" as used herein refers to a kit used to detect the presence or absence of DNA from 3272 plants in a sample comprising nucleic acid probes and primers of the present invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event 3272", "3272" or "3272 event" as used herein, means the original 3272 transformant and/or progeny of the 3272 transformant and/or plants derived in any way from the original 3272 transformant.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent corn plants not all of which is necessarily expressed in the descendant corn plants. The 3272 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the present invention, to a strand of genomic DNA from corn event, 3272. The genomic DNA of 3272 can be from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length. Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the present invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* (5$^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the present invention include hybridization in 7% SDS, 0.25 M NaPO$_4$ pH 7.2 at 67° C. overnight, followed by two washings in 5% SDS, 0.20 M NaPO$_4$ pH7.2 at 65° C. for 30 minutes each wash, and two washings in 1% SDS, 0.20 M NaPO$_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C. The sequences of the present invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a sequence of nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. §1.822 is used herein.

DETAILED DESCRIPTION

This invention relates to a genetically improved line of corn that produces the α-amylase enzyme, Amy797E, and a phosphomannose isomerase enzyme (PMI) that allows the plant to utilize mannose as a carbon source. The invention is particularly drawn to a transgenic corn event designated 3272 comprising a novel genotype, as well as to compositions and methods for detecting nucleic acids from this event in a biological sample. The invention is further drawn to corn plants comprising the 3272 genotype, to transgenic seed from the corn plants, and to methods for producing a corn plant comprising the 3272 genotype by crossing a corn inbred comprising the 3272 genotype with itself or another corn line. Corn plants comprising the 3272 genotype of the invention are useful in the self-processing of starch. Corn plants comprising the 3272 genotype of the invention are also able to utilize mannose as a carbon source.

In one embodiment, the present invention encompasses an isolated nucleic acid molecule comprising at least 10 or more (for example 15, 20, 25, or 50) contiguous nucleotides of a heterologous DNA sequence inserted into the corn plant genome of corn event 3272 and at least 10 or more (for example 15, 20, 25, or 50) contiguous nucleotides of a corn plant genome DNA flanking the point of insertion of a heterologous DNA sequence inserted into the corn plant genome of corn event 3272. Also included are nucleotide sequences that comprise 10 or more nucleotides of contiguous insert sequence from event 3272 and at lease one nucleotide of flanking DNA from event 3272 adjacent to the insert sequence. Such nucleotide sequences are diagnostic for event 3272. Nucleic acid amplification of genomic DNA from the 3272 event produces an amplicon comprising such diagnostic nucleotide sequences.

In another embodiment, the invention encompasses an isolated nucleic acid molecule comprising a nucleotide sequence which comprises at least one junction sequence of event 3272 selected from the group consisting of SEQ ID NO: 1 and SEQ ID NO: 2, and complements thereof, wherein a junction sequence spans the junction between a heterologous expression cassette inserted into the corn genome and DNA from the corn genome flanking the insertion site and is diagnostic for the event.

In another embodiment, the present invention encompasses an isolated nucleic acid linking a heterologous DNA molecule to the corn plant genome in corn event 3272 comprising a sequence of from about 11 to about 20 contiguous nucleotides selected from the group consisting of SEQ ID NO: 1, SEQ ID NO: 2, and the complements thereof.

In another embodiment, the invention encompasses an isolated nucleic acid molecule comprising a nucleotide sequence selected from the group consisting of SEQ ID NO: 1, SEQ ID NO: 2, SEQ ID NO: 3, and SEQ ID NO: 4, and the complements thereof.

In one embodiment of the present invention, an amplicon comprising a nucleotide sequence selected from the group consisting of SEQ ID NO: 1, SEQ ID NO: 2, SEQ ID NO: 3, and SEQ ID NO: 4, and the complements thereof is provided.

In another embodiment, the present invention encompasses flanking sequence primers for detecting event 3272. Such flanking sequence primers comprise an isolated nucleic acid sequence comprising at least 10-15 contiguous nucleotides from nucleotides 1-1409 of SEQ ID NO: 3 (arbitrarily designated herein as the 5′ flanking sequence), or the complements thereof. In one aspect of this embodiment the flanking sequence primers are selected from the group consisting of SEQ ID NO: 34, SEQ ID NO: 35, SEQ ID NO: 39, SEQ ID NO: 45, and SEQ ID NO: 48, and the complements thereof.

In another embodiment, the present invention encompasses flanking sequence primers that comprise at least 10-15 contiguous nucleotides from nucleotides 322-1879 of SEQ ID NO: 4 (arbitrarily designated herein as the 3′ flanking sequence), or the complements thereof. In one aspect of this embodiment the flanking sequence primers are selected from the group consisting of SEQ ID NO: 36 and SEQ ID NO: 42, and the complements thereof.

In still another embodiment, the present invention encompasses a pair of polynucleotide primers comprising a first polynucleotide primer and a second polynucleotide primer which function together in the presence of a corn event 3272 DNA template in a sample to produce an amplicon diagnostic for the corn event 3272, wherein the first primer sequence is or is complementary to a corn plant genome flanking the point of insertion of a heterologous DNA sequence inserted into the corn plant genome of corn event 3272, and the second polynucleotide primer sequence is or is complementary to the heterologous DNA sequence inserted into the corn plant genome of the corn event 3272.

In one aspect of this embodiment the first polynucleotide primer comprises at least 10 contiguous nucleotides from position 1-1409 of SEQ ID NO: 3 or complements thereof. In a further aspect of this embodiment, the first polynucleotide primer comprises the nucleotide sequence set forth in SEQ ID NO: 34, SEQ ID NO: 35, SEQ ID NO: 39, SEQ ID NO: 45, or SEQ ID NO: 48, or complements thereof. In another aspect of this embodiment the first polynucleotide primer comprises at least 10 contiguous nucleotides from position 322-1879 of SEQ ID NO: 4 or complements thereof. In another aspect of this embodiment, the first polynucleotide primer comprises the nucleotide sequence set forth in SEQ ID NO: 36 or SEQ ID NO: 42, or complements thereof. In yet another aspect of this embodiment, the second polynucleotide primer comprises at least 10 contiguous nucleotides of SEQ ID NO: 33, or complements thereof. In still a further aspect of this embodiment, the second polynucleotide primer comprises the nucleotide sequence set forth in SEQ ID NO: 16 to SEQ ID NO: 27, SEQ ID NO: 40, SEQ ID NO: 41, SEQ ID NO: 46, or SEQ ID NO: 49, or complements thereof.

In another aspect of this embodiment, the first polynucleotide primer, which is set forth in SEQ ID NO: 34, and the second polynucleotide primer which is set forth in SEQ ID NO: 21, function together in the presence of a corn event 3272 DNA template in a sample to produce an amplicon diagnostic for the corn event 3272 as described in Example 5. In a further aspect of this embodiment, the first polynucleotide primer, which is et forth in SEQ ID NO: 35, and the second polynucleotide primer, which is set forth in SEQ ID NO: 26, function together in the presence of a corn event 3272 DNA template in a sample to produce an amplicon diagnostic for the corn event 3272 as described in Example 5. In yet another aspect of this embodiment, the first polynucleotide primer, which is set forth in SEQ ID NO: 39, and the second polynucleotide primer, which is set forth in SEQ ID NO: 40, function together in the presence of a corn event 3272 DNA template in a sample to produce an amplicon diagnostic for the corn event 3272 as described in Example 4. In another aspect of this embodiment, the first polynucleotide primer, which is set forth in SEQ ID NO: 45, and the second polynucleotide primer, which is set forth in SEQ ID NO: 46, function together in the presence of corn event 3272 DNA template in a sample to produce an amplicon diagnostic for the corn event 3272 as described in Example 8. In still another aspect of this embodiment, the first polynucleotide primer, which is set forth in SEQ ID NO: 48, and the second polynucleotide primer, which is set forth in SEQ ID NO: 49, function together in the presence of corn event 3272 DNA template in a sample to produce an amplicon diagnostic for the corn event 3272 as described in Example 8.

In another aspect of this embodiment, the first polynucleotide primer, which is set forth in SEQ ID NO: 36, and the second polynucleotide primer which is set forth in SEQ ID NO: 27, function together in the presence of a corn event 3272 DNA template in a sample to produce an amplicon diagnostic for the corn event 3272 as described in Example 5. In still another aspect of this embodiment, the first polynucleotide primer, which is set forth in SEQ ID NO: 42, and the second polynucleotide primer, which is set forth in SEQ ID NO: 41, function together in the presence of a corn event 3272 DNA template in a sample to produce an amplicon diagnostic for the corn event 3272 as described in Example 4.

Of course, it is well within the skill in the art to obtain additional sequence further out into the genome sequence flanking either end of the inserted heterologous DNA sequences for use as a primer sequence that can be used in such primer pairs for amplifying the sequences that are diagnostic for the 3272 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 3 or SEQ ID NO: 4 depending upon the nature of the product desired to be obtained through the use of the nested set of primers intended for use in amplifying a particular flanking sequence containing the junction between the genomic DNA sequence and the inserted heterologous DNA sequence.

In another embodiment, the present invention encompasses a method of detecting the presence of DNA corresponding to the event 3272 in a biological sample, wherein the method comprises: (a) contacting the sample comprising DNA with a probe that hybridizes under high stringency conditions with genomic DNA from corn event 3272 and does not hybridize under high stringency conditions with DNA of a control corn plant; (b) subjecting the sample and probe to high stringency hybridization conditions; and (c) detecting hybridization of the probe to the DNA. In one aspect of this embodiment the amplicon comprises a nucleotide sequence selected from the group consisting of SEQ ID NO: 1, SEQ ID NO: 2, SEQ ID NO: 3, and SEQ ID NO: 4, and compliments thereof.

In another embodiment, the present invention encompasses a method of detecting the presence of a DNA corresponding to the 3272 event in a biological sample, wherein the method comprises: (a) contacting the sample comprising DNA with a probe that hybridizes under high stringency conditions with genomic DNA from corn event 3272 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the 3272 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the present invention encompasses a kit for detecting the presence of 3272 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for event 3272, and other materials necessary to enable nucleic acid hybridization or amplification. A variety of detection methods can be used including TAQMAN (Perkin Elmer), thermal amplification, ligase chain reaction, southern hybridization, ELISA methods, and colorimetric and fluorescent detection methods. In particular the present invention provides for kits for detecting the presence of the target sequence, i.e., at least one of the junctions of the insert DNA with the genomic DNA of the corn plant in 3272, in a sample containing genomic nucleic acid from 3272. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in 3272, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the present invention encompasses a method for detecting event 3272 protein in a biological sample, the method comprising: (a) extracting protein from a sample of corn event 3272 tissue; (b) assaying the extracted protein using an immunological method comprising antibody specific for the insecticidal or selectable marker protein produced by the 3272 event; and (c) detecting the binding of said antibody to the insecticidal or selectable marker protein.

Another embodiment of the present invention encompasses a corn plant, or parts thereof, comprising the genotype of the transgenic event 3272, wherein the genotype comprises the nucleotide sequence set forth in SEQ ID NO: 1, SEQ ID NO: 2, SEQ ID NO: 3, or SEQ ID NO: 4, or complements thereof. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP911, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the 3272 genotype can be introgressed into any plant variety that can be bred with corn, including wild maize species, and thus the preferred inbred lines of this embodiment are not meant to be limiting.

In another embodiment, the present invention encompasses a corn plant comprising at least a first and a second DNA sequence linked together to form a contiguous nucleotide sequence, wherein the first DNA sequence is within a junction sequence and comprises at least about 11 contiguous nucleotides selected from the group consisting of nucleotides 1400-1419 of SEQ ID NO: 3; nucleotides 312-331 of SEQ ID NO: 4; SEQ ID NO: 5; SEQ ID NO: 6; and the complements thereof, wherein the second DNA sequence is within the heterologous insert DNA sequence set forth in SEQ ID NO: 33, and the complements thereof; and wherein the first and the second DNA sequences are useful as nucleotide primers or probes for detecting the presence of corn event 3272 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2

Corn plants of the invention can be further characterized in that digesting the plant's genomic DNA with the restriction endonuclease KpnI results in a single amy797E hybridizing band using a amy797E-specific probe under high stringency conditions. Exemplified herein is a amy797E probe comprising nucleotides 889-2771 of SEQ ID NO: 33.

Corn plants of the invention can be further characterized in that digesting the plant's genomic DNA with the restriction endonuclease XmnI results in a single pmi hybridizing band using a pmi-specific probe under high stringency conditions. Exemplified herein is a pmi probe comprising nucleotides 4506-5681 of SEQ ID NO: 33.

In one embodiment, the present invention provides a corn plant, wherein the 3272 genotype confers upon the corn plant a self-processing capability to hydrolyze starch or the ability to utilize mannose. In one aspect of this embodiment, the genotype conferring the capability to hydrolyze starch upon the corn plant comprises a amy797E gene. In another aspect of this embodiment, the genotype conferring upon the corn plant the ability to utilize mannose comprises a pmi gene.

In one embodiment, the present invention provides a biological sample derived from a event 3272 corn plant, tissue, or seed, wherein the sample comprises a nucleotide sequence which is or is complementary to a sequence selected from the group consisting of SEQ ID NO: 1, and SEQ ID NO: 2, and wherein the sequence is detectable in the sample using a nucleic acid amplification or nucleic acid hybridization method. In one aspect of this embodiment, the sample is selected from corn flour, corn syrup, corn oil, cornstarch, and cereals manufactured in whole or in part to contain corn products.

In another embodiment, the present invention provides an extract derived from a event 3272 corn plant, tissue, or seed comprising a nucleotide sequence which is or is complementary to a nucleotide sequence selected from the group consisting of SEQ ID NO: 1, and SEQ ID NO: 2. In one aspect of this embodiment, the sequence is detected in the extract using a nucleic acid amplification or nucleic acid hybridization method. In another aspect of this embodiment, the sample is selected from corn flour, corn syrup, corn oil, corn starch, and cereals manufactured in whole or in part to contain corn products.

In yet another embodiment, the present invention provides a method for producing a corn plant resistant to at least corn rootworm infestation comprising: (a) sexually crossing a first parent corn plant with a second parent corn plant, wherein said first or second parent corn plant comprises corn event 3272 DNA, thereby producing a plurality of first generation progeny plants; (b) selecting a first generation progeny plant that is self processing; (c) selfing the first generation progeny plant, thereby producing a plurality of second generation progeny plants; and (d) selecting from the second generation progeny plants, a plant that is at least resistant to corn rootworm infestation; wherein the second generation progeny plants comprise a nucleotide sequence selected from the group consisting of SEQ ID NO: 1, and SEQ ID NO: 2.

In another embodiment, the present invention provides a method of producing hybrid corn seeds comprising: (a) planting seeds of a first inbred corn line comprising a nucleotide sequence selected from the group consisting of SEQ ID NO: 1, SEQ ID NO: 2, SEQ ID NO: 3, and SEQ ID NO: 4, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The present invention also encompasses the hybrid seed produced by the embodied method and hybrid plants grown from the seed.

One skilled in the art will recognize that the transgenic genotype of the present invention can be introgressed by breeding into other corn lines comprising different transgenic genotypes. For example, a corn inbred comprising the transgenic genotype of the present invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the present invention include, the glyphosate tolerant GA21 event, the glyphosate tolerant/lepidopteran insect resistant MON802 event, the lepidopteran resistant DBT418 event, the male sterile event MS3, the phosphinothricin tolerant event B16, the lepidopteran insect resistant event MON 80100, the phosphinothricin tolerant events T14 and T25, the lepidopteran insect resistant event 176, and the coleopteran resistant event MON863, all of which are known in the art. It will be further recognized that other combinations can be made with the transgenic genotype of the invention and thus these examples should not be viewed as limiting.

One skilled in the art will also recognize that transgenic corn seed comprising the transgenic genotype of the present invention can be treated with various seed-treatment chemicals.

Breeding

The transgenic genotype of the present invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (Zea mays L.), often referred to as corn, can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids.

Plant breeding techniques known in the art and used in a corn plant breeding program include, but are not limited to, recurrent selection, backcrossing, pedigree breeding, restriction length polymorphism enhanced selection, genetic marker enhanced selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_{.5}$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). A three-way cross hybrid is produced from three inbred lines where two of the inbred lines are crossed (A×B) and then the resulting $F_1$ hybrid is crossed with the third inbred (A×B)×C. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

Typically these self-pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. Through these technologies, the homozygosity of the self-pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

As is readily apparent to one skilled in the art, the foregoing are only some of the various ways by which the inbred of the present invention can be obtained by those looking to introgress the transgenic genotype of the invention into other corn lines. Other means are available, and the above examples are illustrative only.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual*, 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Transformation and Selection of the 3272 Event

The 3272 event was produced by *Agrobacterium*-mediated transformation of a proprietary inbred corn (*Zea mays*) line. Immature embryos were transformed essentially as described in Negrotto et al. (Plant Cell Reports 19: 798-803, 2000), using a DNA fragment from plasmid pNOV7013 (SEQ ID NO: 33). Plasmid pNOV7013 comprises tandem expression cassettes. The first expression cassette is comprised of a γ-Zein promoter sequence (Genbank Accession No. X56117) operably linked to a amy797E α-amylase gene, which is further operably linked to the *Zea mays* Intron No. 9 from the phosphoenolpyruvate carboxylase gene (Matsuoka et al. 1989, Euro. J. Biochem. 181:593-598), which is further operably linked to a 35S 3' end transcription termination and polyadenylation sequence (Franck et al. 1980, Cell 21:285-294). The second expression cassette is comprised of a ZmUbiInt promoter from *Zea mays* (Christensen et al. 1992, Plant Mol. Biol. 18:675-689) operably linked to a pmi coding sequence (Genbank Accession No. M15380), further operably linked to a terminator sequence from the nopaline synthase gene of *Agrobacterium tumefaciens* (GenBank Accession No. V00087).

Immature embryos were excised from 8-12 day old ears and rinsed with fresh medium in preparation for transformation. Embryos were mixed with the suspension of Agrobacterium cells harboring the transformation vector pNOV7013, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. Embryos were transferred to culture medium supplemented with cefotaxime (250 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the pmi and amy797E genes, as well as for the absence of the antibiotic resistance spectinomycin (spec) gene. Plants positive for both transgenes, and negative for the spec gene, were transferred to the greenhouse for further propagation. Positive events were identified and screened using insect bioassays against corn rootworm. Insecticidal events were characterized for copy number by TAQMAN analysis. 3272 was chosen for further analysis based on having a single copy of the transgenes, good protein expression as identified by ELISA, and good enzymatic activity.

The $T_0$ 3272 was crossed to inbred corn lines NP911x and NP2222x, creating $T_1$ populations. The $T_1$ plants were self-pollinated to create the BC1 generation, and this process was repeated to create a BC3 or BC4 generation, respectively. Progeny testing of the backcrossed plants was employed to identify homozygous (converted) families. The 3272-converted inbreds were crossed to other elite inbred lines to create hybrids used in further studies.

Example 2

3272 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (adh1) gene (Genbank accession no. AF044295). It will be recognized by the skilled person that other corn genes can be used as endogenous controls. Reactions were multiplexed to simultaneously amplify amy797E and adh1 or pmi and adh1. For each sample, a master mixture was generated by combining 20 µL extracted genomic DNA with 35 µL 2× TAQMAN Universal PCR Master Mix (Applied Biosystems) supplemented with primers to a final concentration of 900 nM each, probes to a final concentration of 100 nM each, and water to a 70 µL final volume. This mixture was distributed into three replicates of 20 µL each in 96-well amplification plates and sealed with optically clear heat seal film (Marsh Bio Products). PCR was run in an ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event 3272 had one copy of the amy797E gene and one copy of the pmi gene.

Examples of suitable primer/probe sequence combinations which were used are:

Example 3

3272 Detection By Southern Blot

Genomic DNA used for southern analysis was isolated from pooled leaf tissue of ten plants representing the backcross six (BC4) generation of 3272 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the amy797E gene and the pmi gene. For the negative segregant controls, DNA was isolated from pooled leaf tissue of five plants representing the BC4 generation of event 3272. These negative segregant plants were individually analyzed using TAQMAN PCR and the assays were negative for the presence of the amy797E gene and the pmi gene, but were, as expected, positive for the assay internal control, the endogenous maize adh gene.

Southern analysis was carried out using conventional molecular biology techniques. Genomic DNA (7.5 µg) was digested with KpnI or XmnI restriction enzymes, which have a single recognition site within the 3272 T-DNA insert. This approach allows for determination of the number of copies of the elements, corresponding to the specific probe used for each Southern, which have been incorporated into 3272. This results in one hybridization band per copy of the element present in 3272. Following agarose gel electrophoresis and alkaline transfer to a Nytran® membrane, hybridizations were carried out using element-specific full-length PCR-generated probes. The probe used in the amy797E and pmi Southern blots comprise nucleotides 889-2771 of SEQ ID NO: 33 and nucleotides 4506-5681 of SEQ ID NO: 33, respectively. The probes were labeled with $^{32}$P via random priming using the Rediprime™ II system (Amersham Biosciences, Cat. No. RPN1633).

The following hybridization conditions were used: 1-2 million cpm/ml are added to PerfectHyb (Sigma) supplemented with 100 µg/ml Calf Thymus DNA (Invitrogen) pre-warmed to 65° C. Hybridization was carried out at 65° C. for 3 hours. [pre-hyb takes place in same solution as above, same temp O/N or for at least one hour], followed by washing 2× in 2×SSC, 0.1% SDS for 20 minutes at 65° C. and 2× in 0.1× SSC, 0.1% SDS for 20 minutes at 65° C.

Included on each Southern were three control samples: (1) DNA from a negative (non-transformed) segregant used to identify any endogenous *Zea mays* sequences that may cross-hybridize with the element-specific probe; (2) DNA from a negative segregant into which is introduced an amount of

| Primer Name | Primer Sequence | SEQ ID NO: |
|---|---|---|
| synAmy1-forward | 5'-CAAGCAGGAGCTCATCAACATG-3' | SEQ ID NO: 7 |
| synAmy1-reverse | 5'-GCCCTGTGGTTGATCACGAT-3' | SEQ ID NO: 8 |
| synAmy1-probe | 5'-TCCGCGATGACCTTGATGCCGTA-3' (5' label = FAM, 3' label = TAMRA) | SEQ ID NO: 9 |
| PMI-forward | 5'-CCGGGTGAATCAGCGTTT-3' | SEQ ID NO: 10 |
| PMI-reverse | 5'-GCCGTGGCCTTTGACAGT-3' | SEQ ID NO: 11 |
| PMI-probe | 5'-TGCCGCCAACGAATCACCGG-3' (5' label = FAM, 3' label = TAMRA) | SEQ ID NO: 12 |
| ZmADH-267 forward | 5'-GAACGTGTGTTGGGTTTGCAT-3' | SEQ ID NO: 13 |
| ZmADH-337 reverse | 5'-TCCAGCAATCCTTGCACCTT-3' | SEQ ID NO: 14 |
| ZmADH-316 probe | 5'-TGCAGCCTAACCATGCGCAGGGTA-3' (5' label = TET, 3' label = TAMRA) | SEQ ID NO: 15 |

KpnI- or XmnI-digested pNOV7013 that is equal to one copy number based on probe length, to demonstrate the sensitivity of the experiment in detecting a single gene copy within the *Zea mays* genome; and (3) Kpnb or XmnI-digested pNOV7013 plasmid that is equal to one copy number based on probe length, as a positive control for hybridization as well as to demonstrate the sensitivity of the experiment.

The hybridization data provide confirmatory evidence to support the TAQMAN PCR analysis that 3272 contains a single copy of the amy797E and pmi genes, and that 3272 does not contain any of the vector backbone sequences present in pNOV7013. As expected for both the amy797E and pmi probes, the KpnI and XmnI digest, respectively resulted in a single hybridization band, demonstrating that a single copy of each gene is present in the 3272 event. Additionally, for the backbone probe lack of hybridization demonstrates the absence of any pNOV7013 vector backbone sequences being incorporated into 3272 during the transformation process.

Example 4

T-DNA Insert Sequencing

The nucleotide sequence of the entire transgene DNA insert present in event 3272 was determined to demonstrate overall integrity of the insert, contiguousness of the functional elements and to detect any individual basepair changes. The 3272 insert was amplified from DNA derived from the BC4 generation as two individual overlapping fragments. Each fragment was amplified using one polynucleotide primer homologous to plant genomic sequences flanking the 3272 insert and one polynucleotide primer homologous to the insert sequence. To generate the 5' fragment, a first polynucleotide primer homologous to the 5' flanking sequence, AmyF1n-5' (SEQ ID NO: 39), was combined with a second polynucleotide primer homologous to the inserted DNA within the ZmUbiInt promoter, AmyF1n-3' (SEQ ID NO: 40). To generate the 3' fragment, a first polynucleotide primer homologous to the 3' flanking sequence, AmyF2-3' (SEQ ID NO: 42), was combined with a second polynucleotide primer homologous to the inserted DNA within the ZmUbiInt promoter, AmyF2-5' (SEQ ID NO: 42).

PCR amplification was carried out using the Expand High Fidelity PCR system (Roche, Cat. No. 1732650) under the following conditions: 95° C. for 5 min, 94° C. for 30 sec., 50-60° C. for 30 sec. for 35 cycles, 72° C. for 2 min., 72° C. for 10 min. and ending at 4° C. The amplicon resulting from the PCR amplification using SEQ ID NO: 39 and SEQ ID NO: 40 is set forth in SEQ ID NO: 43 and comprises the 5' junction sequence (SEQ ID NO: 1). The amplicon resulting from the PCR amplification using SEQ ID NO: 42 and SEQ ID NO: 41 is set forth in SEQ ID NO: 44 and comprises the 3' junction sequence (SEQ ID NO: 2). Each sequencing fragment was individually cloned into the pCR-XL-TOPO® vector (Invitrogen, Cat. No. K4700-20) and three separate clones for each fragment were identified and sequenced. Sequencing was carried out using an ABI3730XL analyzer using ABI Big-Dye® 1.1 or Big Dye 3.1 dGTP (for GC rich templates) chemistry. The sequence analysis was done using the Phred, Phrap, and Consed package from the University of Washington and was carried out to an error rate of less than 1 in 10,000 bases (Ewing and Green, 1998). The final consensus sequence was determined by combining the sequence data from the six individual clones (three for each sequencing fragment) to generate one consensus sequence of the 3272 insert. Alignment was performed using the ClustalW program with the following parameters: scoring matrix blosum55, gap opening penalty 15, gap extension penalty 6.66 (Thompson et al, 1994, Nucleic Acids Research, 22, 4673-4680).

The consensus sequence data for the 3272 T-DNA insert demonstrated that the overall integrity of the insert and contiguousness of the functional elements within the insert as intended in pNOV7013 have been maintained. Sequence analysis revealed that some truncation occurred at the right border (RB) (nucleotides 1-2 of SEQ ID NO: 33) and left border (LB) (nucleotides 6083-6100 of SEQ ID NO: 33) ends of the T-DNA insert during the transformation process that resulted in event 3272. The RB portion of the T-DNA insert was truncated by 23 bp and the LB end of the T-DNA insert was truncated by 7 bp. These deletions have no effect on the efficacy of the T-DNA insert and this phenomenon has been previously observed in *Agrobacterium* transformation (Tinland & Hohn, 1995. Genetic Engineering, 17: 209-229).

Example 5

Analysis of Flanking DNA Sequence

The corn genome DNA sequence flanking the heterologous DNA inserted into the corn plant genome of event 3272 at the right border (designated the 5'-flanking sequence) was determined using the thermal asymmetric interlaced (TAIL-) PCR method as described by Liu et al. (1995, The Plant Journal 8:457-463). This methods utilizes three nested insert specific primers, CT RB-1 5'-TGCGGTTCTGTCAGTTC-CAAACGTA-3' (SEQ ID NO: 18), CT RB-2 5'-AACGT-GACTCCCTTAATTCTCCGCTCATGATCA-3' (SEQ ID NO: 19), and CT RB-3: 5'-GATTGTCGTTTCCCGCCT-TCAGTTTA-3' (SEQ ID NO: 20), in three successive reactions together with a mixture of arbitrary degenerated primers (AD primers). The AD primer mix was comprised of the following primers: MZEAD1: 5'-WGTGNAGSANCG-NAGA-3' (SEQ ID NO: 28), MZEAD2: 5'-WCAGNTGST-NGTNCTG-3' (SEQ ID NO: 29), MZEAD6 5'-STGGNTC-SANCTNTGC-3' (SEQ ID NO: 30), and MZEAD8 5'-NCCGASTSTSGSGTT-3' (SEQ ID NO: 31), where W=A or T, N=A, T, C or G and S=C or G. All PCR reactions contained 0.5 µM of T-DNA specific primers and 2 to 4 µM of AD primers in 2× Jumstrat Readymix Red PCR reagent (Sigma Chemical Co.).

For the primary TAIL PCR reaction, ten ng of 3272 genomic DNA, CT RB-1 and AD mix primers were used in a 10 µl reaction. PCR conditions were as follows: 4° C. for 2 min., 93° C. for 1 min., 95° C. for 1 min., 94° C. for 30 sec., 62° C. for 1 min., 72° C. for 2 min and 30 sec., 94° C. for 30 sec for 4 more cycles, 94° C. for 30 sec., 25° C. for 3 min., Ramp at 0.2° C. per second to 72° C., 72° C. for 2 min and 30 sec., 94° C. for 10 sec., 68° C. for 1 min., 72° C. for 2 min and 30 sec., 94° C. for 10 sec., 68° C. for 1 min., 72° C. for 2 min and 30 sec., 94° C. for 10 sec., 44° C. for 1 min., 72° C. for 2 min and 30 sec., 94° C. for 10 sec., for 14 more cycles, 72° C. for 5 min., ending at 4° C.

For the secondary TAIL PCR reaction, one µl of the PCR product from the primary reaction was dilute 100-fold with distilled water. Five µl of the diluted product was used as the template in a 50 µl using CT RB-2 and AD mix primers. Conditions for the secondary TAIL PCR reaction were as follows: 4° C. for 2 min., 94° C. for 10 sec., 64° C. for 1 min., 72° C. for 2 min and 30 sec., 94° C. for 10 sec. for 4 more cycles., 94° C. for 10 sec., 64° C. for 1 min., 72° C. for 2 min and 30 sec., 94° C. for 10 sec., 64° C. for 1 min., 72° C. for 2 min and 30 sec., 94° C. for 10 sec., 44° C. for 1 min., 72° C. for 2 min and 30 sec., 94° C. for 10 sec. for 14 more cycles, 94 degrees for 10 sec., 44 degrees for 1 min., 72 degrees for 3 min., 94° C. for 10 sec. for 4 more cycles, 72° C. for 5 min., ending at 4° C.

For the third TAIL PCR reaction, 5 ml of a 100-fold dilution of the secondary PCR product was used as the template in a 50 ml reaction using CT RB-3 and the AD mix primers. Conditions for the third TAIL PCR reaction were as follows: 4° C. for 2 min., 94° C. for 10 sec., 44° C. for 1 min., 72° C. for 2 min. 30 sec., 94° C. for 10 sec. for 19 more cycles, 72° C. for 5 min., ending at 4° C.

After all PCR reactions were completed, agarose gel electrophoresis was performed on the resulting amplicons. The amplicon was excised and purified with QiaAquik Gel Extraction Kit (Cat #: 28706) and sequenced using the corresponding T-DNA primer. The 5' flanking sequence was confirmed by using a primer located in the 5' flanking sequence, 15B13RB1F: 5'-TGCCAAGCCATGCCCATG-CAAGTCG-3' (SEQ ID NO: 34), and a T-DNA specific primer, RB-Pr1a: 5'-GCGGTTCTGTCAGTTCCAAACG-3' (SEQ ID NO: 21), to perform PCR. The PCR reaction generated a 461 bp amplicon comprising nucleotides 1081-1541 of SEQ ID NO: 3, which comprises the 5' junction sequence set forth in SEQ ID NO: 1.

More 5' flanking DNA sequence, further out into the genome beyond that which was described above, and the corn genome DNA sequence flanking the heterologous DNA at the left border (designated the 3'-flanking sequence) was obtained using GenomeWalker™ technology (Clonetech Laboratories, Inc.) in accordance with the manufacturer's instructions. A library was made by digesting 2.5 µg of event 3272 genomic DNA with StuI restriction endonuclease. The resulting genomic DNA fragments were then ligated to the provided GenomeWalker™ adapter, which contains the sequences of the outer and nested adaptor primers. Each ligation was then amplified in a primary PCR reaction using the outer GenomeWalker™ primer (5'-GTAATACGACT-CACTATAGGGC-3'; SEQ ID NO: 32) and an insert-specific primer for either the right border sequence (5'-GTTGCGGT-TCTGTCAGTTCCAAACGTAAA-3'; SEQ ID NO: 22) or left border sequence (5'-TTTCTTAAGATTGAATCCTGT-TGCCGGTCT-3'; SEQ ID NO: 23). The primary PCR product mixture was then diluted and used as a template for a secondary or nested PCR using the nested adaptor primer (5'-ACTATAGGGCACGCGTGGT-3'; SEQ ID NO: 33) provided by GenomeWalker™ and a nested insert-specific primer for either the right border sequence (5'-CTCCGCT-CATGATCAGATTGTCGTTTC-3'; SEQ ID NO: 24) or left border sequence (5'-TTACTAGATCTGCTAGCCCTGCAG-GAAA-3'; SEQ ID NO: 25). The following PCR conditions were used for the primary and secondary reactions: 94° C., 25 s 72° C., 3 min, 7×; 94° C., 25 s; 67° C., 3 min, 32×; 67° C., 7 min, 1×.

The 5' flanking sequence was confirmed using a primer located in the 5' flanking region (SEQ ID NO: 35) combined with an insert sequence primer (SEQ ID NO: 26) in a PCR reaction under the following conditions: 95° C. for 5 min, 94° C. for 30 sec., 50-60° C. for 30 sec. for 35 cycles, 72° C. for 2 min., 72° C. for 10 min. and ending at 4° C. The sequence of the resulting amplicon is set forth in SEQ ID NO: 3, which comprises the 5' junction sequence set forth in SEQ ID NO: 1. The 5' flanking sequence comprised in SEQ ID NO: 3 is set forth in SEQ ID NO: 5.

The 3' flanking sequence was confirmed using a primer located in the 3' flanking region (SEQ ID NO: 36) combined with an insert specific primer (SEQ ID NO: 27) in a PCR reaction under the following conditions: 95° C. for 5 min, 94° C. for 30 sec., 50-60° C. for 30 sec. for 35 cycles, 72° C. for 2 min., 72° C. for 10 min. and ending at 4° C. The sequence of the resulting amplicon is set forth in SEQ ID NO: 4, which comprises the 3' junction sequence set forth in SEQ ID NO: 2. The 3' flanking sequence comprised in SEQ ID NO: 4 is set forth in SEQ ID NO: 6.

Example 6

Analysis of Seed From 3272 Maize Plants Expressing the Amy797E α-Amylase

Seed from 3272 maize plants transformed with pNOV7013 as described in Example 1 was obtained. Starch accumulation in these kernels appeared to be normal, based on visual inspection and on normal staining for starch with an iodine solution prior to any exposure to high temperature. Immature kernels were dissected and purified endosperms were placed individually in microfuge tubes and immersed in 200 µl of 50 mM NaPO$_4$ buffer. The tubes were placed in an 85° C. water bath for 20 minutes, then cooled on ice. Twenty microliters of a 1% iodine solution was added to each tube and mixed. Approximately 25% of the segregating kernels stained normally for starch. The remaining 75% failed to stain, indicating that the starch had been degraded into low molecular weight sugars that do not stain with iodine. It was found that the kernels of 3272 were self-hydrolyzing the corn starch. There was no detectable reduction in starch following incubation at 37° C.

Expression of the amylase was further analyzed by isolation of the hyperthermophilic protein fraction from the endosperm followed by PAGE/Coomassie staining. A segregating protein band of the appropriate molecular weight (50 kD) was observed. These samples are subjected to an α-amylase assay using commercially available dyed amylose (AMYLAZYME, from Megazyme, Ireland). High levels of hyperthermophilic amylase activity correlated with the presence of the 50 kD protein.

Kernels from wild type plants or 3272 plants were heated at 100° C. for 1, 2, 3, or 6 hours and then stained for starch with an iodine solution. Little or no starch was detected in mature kernels after 3 or 6 hours, respectively. Thus, starch in mature kernels from transgenic maize which express hyperthermophilic α-amylase that is targeted to the endoplasmic reticulum was hydrolyzed when incubated at high temperature.

In another experiment, partially purified starch from mature kernels from 3272 plants that were steeped at 50° C. for 16 hours was hydrolyzed after heating at 85° C. for 5 minutes. This illustrated that the α-amylase targeted to the endoplasmic reticulum binds to starch after grinding of the kernel, and is able to hydrolyze the starch upon heating. Iodine staining indicated that the starch remains intact in mature seeds after the 16 hour steep at 50° C.

In another experiment, segregating, mature kernels from 3272 plants were heated at 95° C. for 16 hours and then dried. In seeds expressing the hyperthermophilic α-amylase, the hydrolysis of starch to sugar resulted in a wrinkled appearance following drying.

Example 7

Fermentation of Grain From Maize Plants Expressing α-Amylase

Transgenic 3272 corn that contains a thermostable α-amylase performs well in fermentation without addition of exogenous α-amylase, requires much less time for liquefaction and results in more complete solubilization of starch. Laboratory scale fermentations were performed by a protocol with the following steps (detailed below): 1) grinding, 2) moisture analysis, 3) preparation of a slurry containing ground corn, water, backset and α-amylase, 4) liquefaction and 5) simultaneous saccharification and fermentation (SSF). In this example the temperature and time of the liquefaction step were varied as described below. In addition the transgenic corn was liquefied with and without exogenous α-amylase and the performance in ethanol production compared to control corn treated with commercially available α-amylase.

The corn was dried to 11% moisture and stored at room temperature. The α-amylase content of the 3272 corn flour was 95 units/g where 1 unit of enzyme generates 1 micromole reducing ends per min from corn flour at 85° C. in pH 6.0 MES buffer. The control corn that was used was a yellow dent corn known to perform well in ethanol production. 1) Grinding: Transgenic corn (1180 g) was ground in a Perten 3100 hammer mill equipped with a 2.0 mm screen thus generating transgenic corn flour. Control corn was ground in the same mill after thoroughly cleaning to prevent contamination by the transgenic corn. 2) Moisture analysis: Samples (20 g) of transgenic and control corn were weighed into aluminum weigh boats and heated at 100 C for 4 h. The samples were weighed again and the moisture content calculated from the weight loss. The moisture content of transgenic flour was 9.26%; that of the control flour was 12.54%. 3) Preparation of slurries: The composition of slurries was designed to yield a mash with 36% solids at the beginning of SSF. Control samples were prepared in 100 ml plastic bottles and contained 21.50 g of control corn flour, 23 ml of de-ionized water, 6.0 ml of backset (8% solids by weight), and 0.30 ml of a commercially available α-amylase diluted 1/50 with water. The α-amylase dose was chosen as representative of industrial usage. When assayed under the conditions described above for assay of the transgenic α-amylase, the control α-amylase dose was 2 U/g corn flour. pH was adjusted to 6.0 by addition of ammonium hydroxide. Transgenic samples were prepared in the same fashion but contained 20 g of corn flour because of the lower moisture content of transgenic flour. Slurries of transgenic flour were prepared either with α-amylase at the same dose as the control samples or without exogenous α-amylase. 4) Liquefaction: The bottles containing slurries of transgenic corn flour were immersed in water baths at either 85° C. or 95° C. for times of 5, 15, 30, 45 or 60 min Control slurries were incubated for 60 min at 85° C. During the high temperature incubation the slurries were mixed vigorously by hand every 5 min. After the high temperature step the slurries were cooled on ice. 5) Simultaneous saccharification and fermentation: The mash produced by liquefaction was mixed with glucoamylase (0.65 ml of a 1/50 dilution of a commercially available L-400 glucoamylase), protease (0.60 ml of a 1,000-fold dilution of a commercially available protease), 0.2 mg Lactocide & urea (0.85 ml of a 10-fold dilution of 50% Urea Liquor). A hole was cut into the cap of the 100 ml bottle containing the mash to allow $CO_2$ to vent. The mash was then inoculated with yeast (1.44 ml) and incubated in a water bath set at 90 F. After 24 hours of fermentation the temperature was lowered to 86 F; at 48 hours it was set to 82 F.

Yeast for inoculation was propagated by preparing a mixture that contained yeast (0.12 g) with 70 grams maltodextrin, 230 ml water, 100 ml backset, glucoamylase (0.88 ml of a 10-fold dilution of a commercially available glucoamylase), protease (1.76 ml of a 100-fold dilution of a commercially available enzyme), urea (1.07 grams), penicillin (0.67 mg) and zinc sulfate (0.13 g). The propagation culture was initiated the day before it was needed and was incubated with mixing at 90° F.

At 24, 48 & 72 hour samples were taken from each fermentation vessel, filtered through 0.2 μm filters and analyzed by HPLC for ethanol & sugars. At 72 h samples were analyzed for total dissolved solids and for residual starch.

HPLC analysis was performed on a binary gradient system equipped with refractive index detector, column heater & Bio-Rad Aminex HPX-87H column. The system was equilibrated with 0.005 M $H_2SO_4$ in water at 1 ml/min. Column temperature was 50° C. Sample injection volume was 5 μl; elution was in the same solvent. The RI response was calibrated by injection of known standards. Ethanol and glucose were both measured in each injection.

Residual starch was measured as follows. Samples and standards were dried at 50° C. in an oven, then ground to a powder in a sample mill. The powder (0.2 g) was weighed into a 15 ml graduated centrifuge tube. The powder was washed 3 times with 10 ml aqueous ethanol (80% v/v) by vortexing followed by centrifugation and discarding of the supernatant. DMSO (2.0 ml) was added to the pellet followed by 3.0 ml of a thermostable alpha-amylase (300 units) in MOPS buffer. After vigorous mixing, the tubes were incubated in a water bath at 85° C. for 60 min. During the incubation, the tubes were mixed four times. The samples were cooled and 4.0 ml sodium acetate buffer (200 mM, pH 4.5) was added followed by 0.1 ml of glucoamylase (20 U). Samples were incubated at 50° C. for 2 hours, mixed, then centrifuged for 5 min at 3,500 rpm. The supernatant was filtered through a 0.2 um filter and analyzed for glucose by the HPLC method described above. An injection size of 50 μl was used for samples with low residual starch (<20% of solids).

Event 3272 corn performed well in fermentation without added α-amylase. The yield of ethanol at 72 hours was essentially the same with or without exogenous α-amylase. These data also show that a higher yield of ethanol is achieved when the liquefaction temperature is higher; the present enzyme expressed in the transgenic corn has activity at higher temperatures than other enzymes used commercially such as the *Bacillus liquefaciens* α-amylase.

Example 8

Event 3272-Specific TAQMAN Assay

This example describes an event-specific real-time quantitative TAQMAN PCR method for determination of the relative content of Event 3272 DNA to total maize DNA in a sample. The PCR assay was optimized for use in an ABI Prism® 7900 sequence detection system. Equipment that can be used in this procedure includes but is not limited to: ABI Prism® 7000 sequence detection system (Applied Biosystems Part No. 4339940); Software: Sequence Detection System version 1.1 (Applied Biosystems Part No. 4349157); ABIPrisma$^{tm}$ 7900HT sequence detection system (Applied Biosystems Part No. 4329002 or 4329004); Software: Sequence Detection System version 2.0 (Applied Biosystems Part No. 4329002); Software: Sequence Detection System version 2.1 (Applied Biosystems Part No.43195666); MicroAmp® optical 96-well reaction plates (Applied Biosystems Part No. N801-0560); MicroAmp® optical caps (8 caps/strip) (Applied Biosystems Part No. N801-0935); ABI Prisma® optical adhesive covers (Applied Biosystems Part No. 4311971); ABI Prism® optical adhesive cover starter kit (Applied Biosystems Part No. 4313663); ABI Prism® optical cover compression pads (Applied Biosystems Part No. 4312639).

For specific detection of Event 3272 genomic DNA, a 94-bp fragment of the region that spans the insert-to-plant junction in maize Event 3272 was amplified using two specific primers. PCR products were measured during each cycle (real-time) by means of a target-specific oligonucleotide probe labeled with two fluorescent dyes: FAM as a reporter dye at its 5' end and TAMRA as a quencher dye at its 3' end. The 5'-nuclease activity of the Taq DNA polymerase is exploited, which results in the specific cleavage of the probe, leading to increased fluorescence, which is then monitored.

For relative quantification of Event 3272 DNA, a maize-specific reference system which amplifies a 136-bp fragment of Alcohol Dehydrogenase (Adh1), a maize endogenous gene, using a pair of Adh1 gene-specific primers and an Adh1 gene-specific probe labeled with VIC as a reporter dye at its 5' end and TAMRA as a quencher dye at its 3' end as described above.

Examples of suitable primer/probe sequence combinations which were used in this procedure include:

| Primer Name | Primer Sequence | SEQ ID NO: |
|---|---|---|
| Es3272-5'Forward | 5'-TCATCAGACCAGATTCTCTTTTATGG-3' | SEQ ID NO: 45 |
| Es3272-5'Reverse | 5'-CGTTTCCCGCCTTCAGTTTA-3' | SEQ ID NO: 46 |
| Es3272-5'Probe | 5'-ACTGCTGACGCGGCCAAACACTG-3' (5' label = 6-FAM, 3' label = TAMRA) | SEQ ID NO: 47 |
| ESPCR0026 F | 5'-CATGATGAGTGCGTGATGAGGGCTCTT-3' | SEQ ID NO: 48 |
| ESPCR0004 R | 5'-GTATGATCTCGGCATGACTCACCGTGTT-3' | SEQ ID NO: 49 |
| ZmAdh1 Forward | 5'-CGTCGTTTCCCATCTCTTCCTCC-3' | SEQ ID NO: 50 |
| ZmAdh1 Reverse | 5'-CCACTCCGAGACCCTCAGTC-3' | SEQ ID NO: 51 |
| ZmAdh1 Probe | 5'-AATCAGGGCTCATTTTCTCGCTCCTCA-3' (5' label = VIC, 3' label = TAMRA) | SEQ ID NO: 52 |

For analysis of maize samples, approximately 250 ng of template DNA per reaction was used.

All reagents were allowed to thaw, mix well and store on ice. Two reaction mixes, one for Event 3272 PCR and one for *Zea mays* Adh1 PCR, were prepared. The mastermixes consist of all the components of the PCR, except DNA template, in sufficient quantities for all reactions to be performed (including those for standard DNA solutions). Typically an excess of each mastermix was prepared to account for loss during repeated liquid transfer.

A listing of reagents, buffers and solutions used in this procedure are shown in Tables 1-5.

TABLE 1

List of reagents.

| Reagent | Number/Specification |
|---|---|
| 0.5 M EDTA | Sigma Cat. No. E-7889 |
| Nuclease-free water | Sigma Cat. No. W-4502 |
| PCR primers (10 μM) and fluorescent oligonucleotide probes (5 μM) | Synthesized by Applied Biosystems |
| Sigma Jumpstart RedTaq PCR master mix (2X) requires Supplement (see below) | Sigma Aldrich Ltd P-2893 |
| 1 M Tris-HCl, pH 8.0 | Sigma Cat. No. T-3038 |
| 1 M MgCl$_2$ | |
| Sulforhodamine 101 | Sigma Cat. No. S-7635 |

TABLE 2

50x Zm Adh1 endogenous assay stock.
50x Zm Adh1 Endogenous Assay Stock
1X concentration of primers and probe 300 nM F,
300 nM R, 200 nM Probe For 1 mL of 50X concentration, in an Amber Eppendorf-style tube, mix:

15 μl of Forward Primer (1000 pmol/μl),
15 μl of Reverse Primer (1000 pmol/μl),
100 μl of Probe (100 pmol/μl) and
870 μl nuclease-free water
Vortex well & Store at 4° C. for up to 1 year.

TABLE 3

50x Event 3272 assay stock.
50x Event 3272 Assay Stock
1X concentration of primers and probe 50 nM F,
900 nM R, 200 nM Probe For 1 mL of 50X concentration, in an Amber Eppendorf-style tube, mix:

2.5 μl of Forward Primer (1000 pmol/μl),
45 μl of Reverse Primer (1000 pmol/μl),
100 μl of Probe (100 pmol/μl) and
852.5 μl nuclease-free water
Vortex well & Store at 4° C. for up to 1 year.

TABLE 4

1000x Sulforhodamine 101 stock.
10000x Sulforhodamine 101 Stock

Resuspend 100 mg of Sulforhodamine 101 in 360 ml nuclease free water
Vortex well & Store at −20° C.

TABLE 5

Supplemented 2x Jumpstart Readymix.
Supplemented 2x Jumpstart Readymix
50 ml

To 2x Mastermix, Add:

550 μl of 1M MgCl$_2$,
10 μl 10000x Sulphorhodamine 101
Vortex well & Store at 4° C. for up to 1 year.

When preparing each reaction mix, reagents were typically added in the order listed in Tables 6 and 7.

TABLE 6

Preparation of the reaction for the Zm Adh1 reference gene assay

| Component | Concentration in reaction | Volume per reaction (μl) |
|---|---|---|
| Sigma Jumpstart Readymix 2X | 1x | 12.5 |
| 50x ZmAdh1 Endogenous Assay Stock (1x concentration = 300 nM F, 300 nM R, 200 nM Probe) | 1x | 0.5 |
| Nuclease free water | # | 7 |
| Template DNA (maximum 250 ng) | # | 5 |
| Total volume: | | 25 |

TABLE 7

Preparation of the reaction for the Event 3272 assay

| Component | Final concentration in PCR | Volume per reaction (μl) |
|---|---|---|
| Sigma Jumpstart Readymix 2X | 1x | 12.5 |
| 50x Event 3272 Assay Stock (1x concentration = 50 nM F, 900 nM R, 200 nM Probe) | 1x | 0.5 |
| Nuclease free water | # | 7 |
| Template DNA (maximum 250 ng) | # | 5 |
| Total volume: | | 25 |

The PCR was run using the cycling conditions listed in Table 8 for both Event 3272 and Zm Adh1 assays.

TABLE 8

PCR Cycling Conditons

| Step | Stage | T °C. | Time (sec) | Data collection | Cycles |
|---|---|---|---|---|---|
| 1 | UNG | 50° C. | 120" | no | 1x |
| 2 | Initial denaturation | 95° C. | 600" | no | 1x |
| 3 | Denaturation | 95° C. | 15" | no | |
| | Amplification | | | | 40x |
| 4 | Annealing & Extension | 60° C. | 60" | yes | |

The standard curve was defined by the regression line generated from seven averaged data points, labeled S1 to S7. The first data point used to establish the standard curve was point S1 and was derived from a template containing 100% Event 3272 genomic DNA (gDNA). Standard curve points S2-S7 were obtained by dilutions of the 100% transgenic (GM) gDNA standard, S1, in 100% non-GM gDNA. The % GM concentration range used to establish the standard curve covers 0% to 100%. The dilution scheme and the corresponding amount of Event 3272 gDNA content in each standard are detailed in Table 9.

TABLE 9

Dilution Scheme and Amount of Event 3272 gDNA.

| | STANDARDS | | | | | | |
|---|---|---|---|---|---|---|---|
| | S1 | S2 | S3 | S4 | S5 | S6 | S7 |
| Total gDNA content per reaction (ng) | 250 | 250 | 250 | 250 | 250 | 250 | 250 |
| Total Event 3272 gDNA content per reaction (ng) | 250 | 25 | 12.5 | 2.5 | 1.25 | 0.25 | 0 |
| Relative % GM Content per reaction | 100 | 10 | 5 | 1 | 0.5 | 0.1 | 0 |
| Dilution Factor | 1 | 10 | 20 | 100 | 200 | 1000 | n/a |

Results of the TAQMAN analysis demonstrated that DNA from event 3272 could be selectively detected and quantitated.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the present invention.

What is claimed is:

1. A biological sample comprising a nucleotide sequence selected from the group consisting of SEQ ID NO:1, SEQ ID NO:2 and full length complements thereof.

2. An amplicon from the biological sample of claim 1, wherein the amplicon comprises a nucleotide sequence selected from the group consisting of SEQ ID NO:1, SEQ ID NO:2 and full length complements thereof.

3. The biological sample of claim 1 wherein the sample is selected from the group consisting of corn flour, corn meal, corn syrup, corn oil, corn starch, and cereals manufactured in whole or in part to contain corn by-products.

4. An extract derived from the biological sample of claim 1, wherein the extract comprises a nucleotide sequence selected from the group consisting of SEQ ID NO: 1, SEQ ID NO: 2, and full length complements thereof.

5. The extract of claim 4 wherein the sequence is detectable in the extract using a nucleic acid amplification or nucleic acid hybridization method.

6. A biological sample derived from a event 3272 corn plant, tissue, or seed, wherein the sample comprises a nucleotide sequence selected from the group consisting of SEQ ID NO:1, and SEQ ID NO:2, and wherein the sequence is detectable in the sample using a nucleic acid amplification or nucleic acid hybridization method.

7. The biological sample of claim 6 wherein the sample is selected from the group consisting of corn flour, corn meal, corn syrup, corn oil, corn starch, and cereals manufactured in whole or in part to contain corn by-products.

* * * * *

SEQUENCE LISTING

<160> NUMBER OF SEQ ID NOS: 52

<210> SEQ ID NO 1
<211> LENGTH: 20
<212> TYPE: DNA
<213> ORGANISM: Zea mays
<220> FEATURE:
<221> NAME/KEY: misc_feature
<222> LOCATION: (1)..(20)
<223> OTHER INFORMATION: 5' junction sequence

<400> SEQUENCE: 1
ctgacgcggc caaacactga                                           20

<210> SEQ ID NO 2
<211> LENGTH: 20
<212> TYPE: DNA
<213> ORGANISM: Zea mays
<220> FEATURE:
<221> NAME/KEY: misc_feature
<222> LOCATION: (1)..(20)
<223> OTHER INFORMATION: 3' junction sequence

<400> SEQUENCE: 2
cacaatatat tcaagtcatc                                           20

```
<210> SEQ ID NO 3
<211> LENGTH: 1600
<212> TYPE: DNA
<213> ORGANISM: Zea mays
<220> FEATURE:
<221> NAME/KEY: misc_feature
<222> LOCATION: (1)..(463)
<223> OTHER INFORMATION: 5' flanking + insert

<400> SEQUENCE: 3
agccaatcac ggcaaaatac gcaagcataa cgcgcggctc acgtctcccc acccgatccc      60
cggccccacg ctaccattta tgaagctctt tcattcatgt tacgtatgca taaacgccgg     120
tacctgcgcg cggtataccc accacctgcc acgtcgaccc gcggcccgca cacctagcca     180
cgccgggggc cggggctctc tctagtaatg gaagccctgg gcttccatta cctcgtccct     240
gcgtgcagct ctcttctgta ctaagatttc atccctgatc ctgcgcgggt catcatcaat     300
acgagacggc catctcatgc atccgtcctc ctctccgatc cctgatctga tggatcattc     360
caacaatatt taatatacta ctctactagc gtcgtgtgta catgtgcctt gtagtactgt     420
actgtacagc tagctagcta gctccgagca gcaaagcagg ctacaggcta ggcagggctt     480
gaagtcgcat tgcattgcat cgcatgcgca tcgcagcatg catcaattcc tgcccagaga     540
gcgaagtgga ttaattaatt agcaccaagg actgtggtac gtactgctgc taaaaactaa     600
aaaggtttga aatgctgaga gagagagaaa gagagagagt acatgcatgc aatgcaatgc     660
accatgcatc tttcaattcc atggcgccgt agcatctctc tctctctata gccttctctt     720
tccatcaacc tgagcaaaag aaagctggtt tcctgcaggc tgcgtgcgcc cggcggccgt     780
ctctgctgcg tgcatgcatc agcatgcgcg cagtaactcc acacagccag cctctcctac     840
aaaagacatg tactacagta ccgctaccga gctagtacta ggtacacaca gtgtgtgtgt     900
gtggctggct actagtgttt cttcttgaac gatgaatata cagcacaatc ctcctgctct     960
cttgctcttg ctcttgcgct gcatgctctt ccttccccgc actccctaat agctaggcat    1020
gcattgtcca ttgaattgaa gctctctctc tctctctctc tctctctctc tctctctctc    1080
tgccaagcca tgcccatgca agtcgtcgtc tctgttccag ctgaattcat gcccatgcaa    1140
atgcaagtcg tacgtctctc tttccagaat tcagcagcag tactctccac gcactgatcg    1200
ccgtcagaga gctaggtcag tggctgcagt gagtgggcat gatgagtgcg tgatgagggc    1260 tctttggag ctactactac tagcgtgtgt attcattcac tctcactggc cgataaactg    1320
accatctatt tatctccaat cgatcgaatt catcagacca gattctcttt tatggccggc    1380
cggccggccc tgctgactgc tgacgcggcc aaacactgat agtttaaact gaaggcggga    1440
aacgacaatc tgatcatgag cggagaatta agggagtcac gttatgaccc ccgccgatga    1500
cgcgggacaa gccgttttac gtttggaact gacagaaccg caacgctgca ggaattggcc    1560
gcagcggcca tttaaatcaa ttgggcgcgc cgaattcgag                           1600

<210> SEQ ID NO 4
<211> LENGTH: 1878
<212> TYPE: DNA
<213> ORGANISM: Zea mays
<220> FEATURE:
<221> NAME/KEY: misc_feature
<222> LOCATION: (1)..(1878)
<223> OTHER INFORMATION: 3' insert + flanking

<400> SEQUENCE: 4
gaatcctgtt gccggtcttg cgatgattat catataattt ctgttgaatt acgttaagca     60
tgtaataatt aacatgtaat gcatgacgtt atttatgaga tgggttttta tgattagagt    120
```

```
cccgcaatta tacatttaat acgcgataga aaacaaaata tagcgcgcaa actaggataa        180
attatcgcgc gcggtgtcat ctatgttact agatctgcta gccctgcagg aaatttaccg        240
gtgcccgggc ggccagcatg gccgtatccg caatgtgtta ttaagttgtc taagcgtcaa        300
tttgtttaca ccacaatata ttcaagtcat ctgcatgtga aataaacatc ttgtccctcc        360
tcgatgatcc acctctctct ctctctctct ctctctctct ctctctctct ctctctctca        420
tgctcaattg ctcatgcata tgcacgcgcg cgtttgctcg cccattgttt gtttgctttt        480
gcttttatgt tcgatcgatg gatgtatgtg tatataggcg agaaggggca ccagctgctg        540
catgcctgtt tcttacagtc ttgtattgta tgcatgcaaa agagagaagc tagactagac        600
cagacaacac tagcgattct gacaggctga cttttgagca gttgactact cgctctacat        660
acagccttgt attattgtat agttttcttt aatgcctgac gttcacgtgt tcctatgcat        720
tgcagtgtat agcgacctgc ctatcgtgga cctttgtttt ttttcaattc tatttgttta        780
atcagatact gtacagtaaa gatgcagact cacaaataaa cacgcatgaa aaaaaggtg         840 ctatccgtct gaacttctga tctacactag tacacagaag ctctatagtg gcagttgaaa        900
acgtatttac actggcgttt ttcagttccg ccagtgctag gggccagtgg aaatcagcat        960
ttccactggc ggttatttg  gaaccgccag tggaaagtgc attttcactg gcggttttct       1020
taaggaaacc gccagtgaaa agtgcatttt caaccgccag tgaaaatgca ctttacactg       1080
gcggtttcct ttataaaacc gccagtggaa atgcactttt cactggcggt tttctttatt       1140
tagccgccag tggaagtttt cccgcctttt ttcaaaattt caaacaatac tgaattatag       1200
atatatttat ttacacacac acaaacatat atatatatag atctatattg atattgaaag       1260
caacatggaa ttaaattcta tcatacattt atatacatca aagtattctg tttacaacca       1320
tatatgcttc atgcattcta tacatcaaaa gttttcacct aagttctaat aactatctcg       1380
gctaagagat aatctactaa ttttttgttag tattctaaac tctggcaaag ctaatgttcc      1440
ggaagcatcg tgatattttc cttctccggg aatgacctct ttcaatatga atgtgcagag       1500
gtcctcgact atgccataca atgcagcttc ggtcaagttc tccgggtttc ctcgttgaaa       1560
ttgctgtaaa ggaattttat aaacatcatc tatttatact caataataac acatttgcat       1620 cttttaatgac ataaatacat acttgactat tactaataat accttgtcag ggttcgtgat      1680
gtatcgtccg ttcactctca tgaactcgca cgcatagaat ccacatagga ccgatccttg       1740
tggttgcttg tggcactaca taacgggaga ttggttattt agttgcaaca ttgtgtatga       1800
tatgtattca taaaatcaca tacttaccgg ccagtgatga tggatgtcta gtggcacgcg       1860
ttgtttcgac aggtcgta                                                     1878
```

<210> SEQ ID NO 5  
<211> LENGTH: 1409  
<212> TYPE: DNA  
<213> ORGANISM: Zea mays  
<220> FEATURE:  
<221> NAME/KEY: misc_feature  
<222> LOCATION: (1)..(1409)  
<223> OTHER INFORMATION: 5' flanking sequence

<400> SEQUENCE: 5

```
agccaatcac ggcaaaatac gcaagcataa cgcgcggctc acgtctcccc acccgatccc         60
cggccccacg ctaccattta tgaagctctt tcattcatgt tacgtatgca taaacgccgg        120
tacctgcgcg cggtataccc accacctgcc acgtcgaccc gcggcccgca cacctagcca        180 cgccggggc cggggctctc tctagtaatg gaagccctgg gcttccatta cctcgtccct        240
```

```
gcgtgcagct ctcttctgta ctaagatttc atccctgatc ctgcgcgggt catcatcaat      300
acgagacggc catctcatgc atccgtcctc ctctccgatc cctgatctga tggatcattc      360
caacaatatt taatatacta ctctactagc gtcgtgtgta catgtgcctt gtagtactgt      420
actgtacagc tagctagcta gctccgagca gcaaagcagg ctacaggcta ggcagggctt      480
gaagtcgcat tgcattgcat cgcatgcgca tcgcagcatg catcaattcc tgcccagaga      540
gcgaagtgga ttaattaatt agcaccaagg actgtggtac gtactgctgc taaaaactaa      600
aaaggtttga aatgctgaga gagagagaaa gagagagagt acatgcatgc aatgcaatgc      660
accatgcatc tttcaattcc atggcgccgt agcatctctc tctctctata gccttctctt      720
tccatcaacc tgagcaaaag aaagctggtt tcctgcaggc tgcgtgcgcc cggcggccgt      780
ctctgctgcg tgcatgcatc agcatgcgcg cagtaactcc acacagccag cctctcctac      840
aaaagacatg tactacagta ccgctaccga gctagtacta ggtacacaca gtgtgtgtgt      900
gtggctggct actagtgttt cttcttgaac gatgaatata cagcacaatc ctcctgctct      960
cttgctcttg ctcttgcgct gcatgctctt ccttccccgc actccctaat agctaggcat     1020
gcattgtcca ttgaattgaa gctctctctc tctctctctc tctctctctc tctctctctc     1080
tgccaagcca tgcccatgca agtcgtcgtc tctgttccag ctgaattcat gcccatgcaa     1140
atgcaagtcg tacgtctctc tttccagaat tcagcagcag tactctccac gcactgatcg     1200
ccgtcagaga gctaggtcag tggctgcagt gagtgggcat gatgagtgcg tgatgagggc     1260
tcttttggag ctactactac tagcgtgtgt attcattcac tctcactggc cgataaactg     1320
accatctatt tatctccaat cgatcgaatt catcagacca gattctcttt tatggccggc     1380
cggccggccc tgctgactgc tgacgcggc                                       1409
```

<210> SEQ ID NO 6
<211> LENGTH: 1557
<212> TYPE: DNA
<213> ORGANISM: Zea mays
<220> FEATURE:
<221> NAME/KEY: misc_feature
<222> LOCATION: (1)..(1557)
<223> OTHER INFORMATION: 3' flanking sequence

<400> SEQUENCE: 6

```
tcaagtcatc tgcatgtgaa ataaacatct tgtccctcct cgatgatcca cctctctctc       60
tctctctctc tctctctctc tctctctctc tctctctcat gctcaattgc tcatgcatat      120
gcacgcgcgc gtttgctcgc ccattgtttg tttgcttttg cttttatgtt cgatcgatgg      180
atgtatgtgt atataggcga gaaggggcac cagctgctgc atgcctgttt cttacagtct      240
tgtattgtat gcatgcaaaa gagagaagct agactagacc agacaacact agcgattctg      300
acaggctgac ttttgagcag ttgactactc gctctacata cagccttgta ttattgtata      360 gttttctttta atgcctgacg ttcacgtgtt cctatgcatt gcagtgtata gcgacctgcc      420
tatcgtggac ctttgttttt tttcaattct atttgtttaa tcagatactg tacagtaaag      480
atgcagactc acaaataaac acgcatgaaa aaaaggtgc tatccgtctg aacttctgat      540
ctacactagt acacagaagc tctatagtgg cagttgaaaa cgtatttaca ctggcgtttt      600
tcagttccgc cagtgctagg ggccagtgga atcagcatt ccactggcg gttatttggg       660 aaccgccagt ggaaagtgca ttttcactgg cggttttctt aaggaaaccg ccagtgaaaa      720
gtgcattttc aaccgccagt gaaatgcac tttacactgg cggtttcctt tataaaaccg       780
ccagtggaaa tgcactttc actggcggtt ttctttattt agccgccagt ggaagttttc       840
```

```
ccgcctttt tcaaaatttc aaacaatact gaattataga tatatttatt tacacacaca    900
caaacatata tatatataga tctatattga tattgaaagc aacatggaat taaattctat    960
catacattta tatacatcaa agtattctgt ttacaaccat atatgcttca tgcattctat   1020
acatcaaaag ttttcaccta agttctaata actatctcgg ctaagagata atctactaat   1080
ttttgttagt attctaaact ctggcaaagc taatgttccg gaagcatcgt gatattttcc   1140
ttctccggga atgacctctt tcaatatgaa tgtgcagagg tcctcgacta tgccatacaa   1200
tgcagcttcg gtcaagttct ccgggtttcc tcgttgaaat tgctgtaaag gaattttata   1260
aacatcatct atttatactc aataataaca catttgcatc tttaatgaca taaatacata   1320
cttgactatt actaataata ccttgtcagg gttcgtgatg tatcgtccgt tcactctcat   1380
gaactcgcac gcatagaatc cacataggac cgatccttgt ggttgcttgt ggcactacat   1440
aacgggagat tggttattta gttgcaacat tgtgtatgat atgtattcat aaaatcacat   1500
acttaccggc cagtgatgat ggatgtctag tggcacgcgt tgtttcgaca ggtcgta      1557
```

```
<210> SEQ ID NO 7
<211> LENGTH: 22
<212> TYPE: DNA
<213> ORGANISM: Artificial Sequence
<220> FEATURE:
<223> OTHER INFORMATION: synAmyl-forward primer

<400> SEQUENCE: 7
caagcaggag ctcatcaaca tg                                              22

<210> SEQ ID NO 8
<211> LENGTH: 20
<212> TYPE: DNA
<213> ORGANISM: Artificial Sequence
<220> FEATURE:
<223> OTHER INFORMATION: synAmyl-reverse primer

<400> SEQUENCE: 8
gccctgtggt tgatcacgat                                                 20

<210> SEQ ID NO 9
<211> LENGTH: 23
<212> TYPE: DNA
<213> ORGANISM: Artificial Sequence
<220> FEATURE:
<223> OTHER INFORMATION: synAmyl probe

<400> SEQUENCE: 9
tccgcgatga ccttgatgcc gta                                             23

<210> SEQ ID NO 10
<211> LENGTH: 18
<212> TYPE: DNA
<213> ORGANISM: Artificial Sequence
<220> FEATURE:
<223> OTHER INFORMATION: pmi TAQMAN Forward Primer

<400> SEQUENCE: 10
ccgggtgaat cagcgttt                                                   18

<210> SEQ ID NO 11
<211> LENGTH: 18
<212> TYPE: DNA
<213> ORGANISM: Artificial Sequence
<220> FEATURE:
<223> OTHER INFORMATION: pmi TAQMAN Reverse Primer
```

-continued

<400> SEQUENCE: 11
gccgtggcct ttgacagt                                              18

<210> SEQ ID NO 12
<211> LENGTH: 20
<212> TYPE: DNA
<213> ORGANISM: Artificial Sequence
<220> FEATURE:
<223> OTHER INFORMATION: pmi TAQMAN Probe

<400> SEQUENCE: 12
tgccgccaac gaatcaccgg                                            20

<210> SEQ ID NO 13
<211> LENGTH: 21
<212> TYPE: DNA
<213> ORGANISM: Artificial Sequence
<220> FEATURE:
<223> OTHER INFORMATION: ZmADH TAQMAN Forward Primer

<400> SEQUENCE: 13
gaacgtgtgt tgggtttgca t                                          21

<210> SEQ ID NO 14
<211> LENGTH: 20
<212> TYPE: DNA
<213> ORGANISM: Artificial Sequence
<220> FEATURE:
<223> OTHER INFORMATION: ZmADH TAQMAN Reverse Primer

<400> SEQUENCE: 14
tccagcaatc cttgcacctt                                            20

<210> SEQ ID NO 15
<211> LENGTH: 24
<212> TYPE: DNA
<213> ORGANISM: Artificial Sequence
<220> FEATURE:
<223> OTHER INFORMATION: ZmADH TAQMAN Probe

<400> SEQUENCE: 15
tgcagcctaa ccatgcgcag ggta                                       24

<210> SEQ ID NO 16
<211> LENGTH: 20
<212> TYPE: DNA
<213> ORGANISM: Artificial Sequence
<220> FEATURE:
<223> OTHER INFORMATION: synAmyl 1894 primer

<400> SEQUENCE: 16
atctccgcga tctggatacc                                            20

<210> SEQ ID NO 17
<211> LENGTH: 20
<212> TYPE: DNA
<213> ORGANISM: Artificial Sequence
<220> FEATURE:
<223> OTHER INFORMATION: synAmyl-2933 primer

<400> SEQUENCE: 17
ccggaggagt acacgtactt                                            20

```
<210> SEQ ID NO 18
<211> LENGTH: 25
<212> TYPE: DNA
<213> ORGANISM: Artificial Sequence
<220> FEATURE:
<223> OTHER INFORMATION: CT RB-1 primer

<400> SEQUENCE: 18
tgcggttctg tcagttccaa acgta                                       25

<210> SEQ ID NO 19
<211> LENGTH: 33
<212> TYPE: DNA
<213> ORGANISM: Artificial Sequence
<220> FEATURE:
<223> OTHER INFORMATION: CT RB-2 Primer

<400> SEQUENCE: 19
aacgtgactc ccttaattct ccgctcatga tca                              33

<210> SEQ ID NO 20
<211> LENGTH: 26
<212> TYPE: DNA
<213> ORGANISM: Artificial Sequence
<220> FEATURE:
<223> OTHER INFORMATION: CT RB-3 Primer

<400> SEQUENCE: 20
gattgtcgtt tcccgccttc agttta                                      26

<210> SEQ ID NO 21
<211> LENGTH: 22
<212> TYPE: DNA
<213> ORGANISM: Artificial Sequence
<220> FEATURE:
<223> OTHER INFORMATION: RB-Pr1a Primer

<400> SEQUENCE: 21
gcggttctgt cagttccaaa cg                                          22

<210> SEQ ID NO 22
<211> LENGTH: 29
<212> TYPE: DNA
<213> ORGANISM: Artificial Sequence
<220> FEATURE:
<223> OTHER INFORMATION: RB GW-insert Primer

<400> SEQUENCE: 22
gttgcggttc tgtcagttcc aaacgtaaa                                   29

<210> SEQ ID NO 23
<211> LENGTH: 30
<212> TYPE: DNA
<213> ORGANISM: Artificial Sequence
<220> FEATURE:
<223> OTHER INFORMATION: LB GW-insert Primer

<400> SEQUENCE: 23
tttcttaaga ttgaatcctg ttgccggtct                                  30

<210> SEQ ID NO 24
<211> LENGTH: 27
<212> TYPE: DNA
<213> ORGANISM: Artificial Sequence
<220> FEATURE:
<223> OTHER INFORMATION: RB Nested Primer
```

```
<400> SEQUENCE: 24
ctccgctcat gatcagattg tcgtttc                                    27

<210> SEQ ID NO 25
<211> LENGTH: 28
<212> TYPE: DNA
<213> ORGANISM: Artificial Sequence
<220> FEATURE:
<223> OTHER INFORMATION: LB Nested Primer

<400> SEQUENCE: 25
ttactagatc tgctagccct gcaggaaa                                   28

<210> SEQ ID NO 26
<211> LENGTH: 18
<212> TYPE: DNA
<213> ORGANISM: Artificial Sequence
<220> FEATURE:
<223> OTHER INFORMATION: AmyRBflank-3'

<400> SEQUENCE: 26
gcgcgcccaa ttgattta                                              18

<210> SEQ ID NO 27
<211> LENGTH: 19
<212> TYPE: DNA
<213> ORGANISM: Artificial Sequence
<220> FEATURE:
<223> OTHER INFORMATION: AmyLBflank-5' primer

<400> SEQUENCE: 27
gaatcctgtt gccggtctt                                             19

<210> SEQ ID NO 28
<211> LENGTH: 16
<212> TYPE: DNA
<213> ORGANISM: Artificial Sequence
<220> FEATURE:
<223> OTHER INFORMATION: MZEAD1 primer
<220> FEATURE:
<221> NAME/KEY: misc_feature
<222> LOCATION: (1)..(16)
<223> OTHER INFORMATION: W = A or T; N = A, C, T or G; S = C or G

<400> SEQUENCE: 28
wgtgnagsan cgnaga                                                16

<210> SEQ ID NO 29
<211> LENGTH: 16
<212> TYPE: DNA
<213> ORGANISM: Artificial Sequence
<220> FEATURE:
<223> OTHER INFORMATION: MZEAD2 primer
<220> FEATURE:
<221> NAME/KEY: misc_feature
<222> LOCATION: (1)..(16)
<223> OTHER INFORMATION: W = A or T; N = A, T, C or G; S = C or G

<400> SEQUENCE: 29
wcagntgstn gtnctg                                                16

<210> SEQ ID NO 30
<211> LENGTH: 16
<212> TYPE: DNA
<213> ORGANISM: Artificial Sequence
<220> FEATURE:
<223> OTHER INFORMATION: MZEAD6 Primer
```

```
<220> FEATURE:
<221> NAME/KEY: misc_feature
<222> LOCATION: (1)..(16)
<223> OTHER INFORMATION: S = C or G; N = A, T, C or G

<400> SEQUENCE: 30
stggntcsan ctntgc                                                              16

<210> SEQ ID NO 31
<211> LENGTH: 15
<212> TYPE: DNA
<213> ORGANISM: Artificial Sequence
<220> FEATURE:
<223> OTHER INFORMATION: MZEAD8 Primer
<220> FEATURE:
<221> NAME/KEY: misc_feature
<222> LOCATION: (1)..(15)
<223> OTHER INFORMATION: S = C or G; N = A, T, C or G

<400> SEQUENCE: 31
nccgaststs gsgtt                                                               15

<210> SEQ ID NO 32
<211> LENGTH: 22
<212> TYPE: DNA
<213> ORGANISM: Artificial Seuqnce
<220> FEATURE:
<223> OTHER INFORMATION: Outer GenomeWalker Primer

<400> SEQUENCE: 32
gtaatacgac tcactatagg gc                                                       22

<210> SEQ ID NO 33
<211> LENGTH: 19
<212> TYPE: DNA
<213> ORGANISM: Artificial Sequence
<220> FEATURE:
<223> OTHER INFORMATION: Nested Adapter Primer

<400> SEQUENCE: 33
actatagggc acgcgtggt                                                           19

<210> SEQ ID NO 34
<211> LENGTH: 24
<212> TYPE: DNA
<213> ORGANISM: Artificial Sequence
<220> FEATURE:
<223> OTHER INFORMATION: 15B13RB1F primer

<400> SEQUENCE: 34
tgccaagcca tgccatgcaa gtcg                                                     24

<210> SEQ ID NO 35
<211> LENGTH: 20
<212> TYPE: DNA
<213> ORGANISM: Artificial Sequence
<220> FEATURE:
<223> OTHER INFORMATION: AmyRBflank-5' primer

<400> SEQUENCE: 35
agccaatcac ggcaaaatac                                                          20

<210> SEQ ID NO 36
<211> LENGTH: 20
<212> TYPE: DNA
<213> ORGANISM: Artificial Sequence
<220> FEATURE:
<223> OTHER INFORMATION: AmyLBflank-3' primer
```

<400> SEQUENCE: 36
tacgacctgt cgaaacaacg                                                   20

<210> SEQ ID NO 37
<211> LENGTH: 6100
<212> TYPE: DNA
<213> ORGANISM: Zea mays
<220> FEATURE:
<221> NAME/KEY: misc_feature
<222> LOCATION: (1)..(2)
<223> OTHER INFORMATION: Right border
<220> FEATURE:
<221> NAME/KEY: misc_feature
<222> LOCATION: (203)..(879)
<223> OTHER INFORMATION: GZein promoter
<220> FEATURE:
<221> NAME/KEY: misc_feature
<222> LOCATION: (889)..(2271)
<223> OTHER INFORMATION: amy797E
<220> FEATURE:
<221> NAME/KEY: misc_feature
<222> LOCATION: (2413)..(2482)
<223> OTHER INFORMATION: 35S terminator
<220> FEATURE:
<221> NAME/KEY: misc_feature
<222> LOCATION: (2501)..(4493)
<223> OTHER INFORMATION: ZmUbiInt promoter
<220> FEATURE:
<221> NAME/KEY: misc_feature
<222> LOCATION: (4506)..(5681)
<223> OTHER INFORMATION: pmi
<220> FEATURE:
<221> NAME/KEY: misc_feature
<222> LOCATION: (5742)..(5994)
<223> OTHER INFORMATION: NOS terminator
<220> FEATURE:
<221> NAME/KEY: misc_feature
<222> LOCATION: (6083)..(6100)
<223> OTHER INFORMATION: Left boder

<400> SEQUENCE: 37
caaacactga tagtttaaac tgaaggcggg aaacgacaat ctgatcatga gcggagaatt    60
aagggagtca cgttatgacc cccgccgatg acgcgggaca agccgtttta cgtttggaac   120
tgacagaacc gcaacgctgc aggaattggc cgcagcggcc atttaaatca attgggcgcg   180
ccgaattcga gctcggtaca agcttcgatc atccaggtgc aaccgtataa gtcctaaagt   240
ggtgaggaac acgaaacaac catgcattgg catgtaaagc tccaagaatt tgttgtatcc   300
ttaacaactc acagaacatc aaccaaaatt gcacgtcaag ggtattgggt aagaaacaat   360
caaacaaatc ctctctgtgt gcaaagaaac acggtgagtc atgccgagat catactcatc   420
tgatatacat gcttacagct cacaagacat tacaaacaac tcatattgca ttacaaagat   480
cgtttcatga aaataaaat aggccggaca ggacaaaaat ccttgacgtg taaagtaaat   540
ttacaacaaa aaaaagcca tatgtcaagc taaatctaat tcgttttacg tagatcaaca   600
acctgtagaa ggcaacaaaa ctgagccacg cagaagtaca gaatgattcc agatgaacca   660
tcgacgtgct acgtaaagag agtgacgagt catatacatt tggcaagaaa ccatgaagct   720
gcctacagcc gtctcggtgg cataagaaca caagaaattg tgttaattaa tcaaagctat   780
aaataacgct cgcatgcctg tgcacttctc catcaccacc actgggtctt cagaccatta   840
gctttatcta ctccagagcg cagaagaacc cgatcgacag gatccaccat gagggtgttg   900
ctcgttgccc tcgctctcct ggctctcgct gcgagcgcca ccagcgctaa gtacctggag   960
ctggaggagg gcgcgtgat catgcaggcg ttctactggg acgtcccgag cggaggcatc  1020
tggtgggaca ccatccgcca gaagatcccc gagtggtacg acgccggcat ctccgcgatc  1080

-continued

```
tggataccgc cagcttccaa gggcatgtcc gggggctact cgatgggcta cgacccgtac    1140
gactacttcg acctcggcga gtactaccag aagggcacgg tggagacgcg cttcgggtcc    1200
aagcaggagc tcatcaacat gatcaacacg gcgcacgcct acggcatcaa ggtcatcgcg    1260
gacatcgtga tcaaccacag gccggcggc gacctggagt ggaacccgtt cgtcggcgac     1320
tacacctgga cggacttctc caaggtcgcc tccggcaagt acaccgccaa ctacctcgac    1380
ttccacccca acgagctgca cgcgggcgac tccggcacgt tcggcggcta cccggacatc    1440
tgccacgaca agtcctggga ccagtactgg ctctgggcct cgcaggagtc ctacgcggcc    1500
tacctgcgct ccatcggcat cgacgcgtgg cgcttcgact acgtcaaggg ctacggggcc    1560
tgggtggtca aggactggct caactggtgg ggcggctggg cggtgggcga gtactgggac    1620
accaacgtcg acgcgctgct caactgggcc tactcctccg cgccaaggt gttcgacttc     1680 cccctgtact acaagatgga cgcggccttc gacaacaaga catcccggc gctcgtcgag     1740 gccctgaaga acgcggcac ggtggtctcc cgcgacccgt tcaaggccgt gaccttcgtc     1800
gccaaccacg acacggacat catctggaac aagtacccgg cgtacgcctt catcctcacc    1860
tacgagggcc agcccacgat cttctaccgc gactacgagg agtggctgaa caaggacaag    1920
ctcaagaacc tgatctggat tcacgacaac ctcgcgggcg gctccactag tatcgtgtac    1980
tacgactccg acgagatgat cttcgtccgc aacggctacg gctccaagcc cggcctgatc    2040
acgtacatca acctgggctc ctccaaggtg ggccgctggg tgtacgtccc gaagttcgcc    2100
ggcgcgtgca tccacgagta caccggcaac ctcggcggct gggtggacaa gtacgtgtac    2160
tcctccggct gggtctacct ggaggcccg gcctacgacc ccgccaacgg ccagtacggc     2220
tactccgtgt ggtcctactg cggcgtcggc tccgagaagg acgagctgtg ataggtaacg    2280
aaactagagc tctagatctg ttctgcacaa agtggagtag tcagtcatcg atcaggaacc    2340
agacaccaga cttttattca tacagtgaag tgaagtgaag tgcagtgcag tgagttgctg    2400 gttttttgtac aacttagtat gtatttgtat ttgtaaaata cttctatcaa taaaatttct    2460
aattcctaaa accaaaatcc aggggtacca gcttgcatgc ctgcagtgca gcgtgacccg    2520
gtcgtgcccc tctctagaga taatgagcat tgcatgtcta agttataaaa aattaccaca    2580 tattttttt gtcacacttg tttgaagtgc agtttatcta tctttataca tatatttaaa    2640
ctttactcta cgaataatat aatctatagt actacaataa tatcagtgtt ttagagaatc    2700
atataaatga acagttagac atggtctaaa ggacaattga gtattttgac aacaggactc    2760
tacagtttta tcttttttagt gtgcatgtgt tctcctttt ttttgcaaat agcttcacct    2820
atataatact tcatccattt tattagtaca tccatttagg gtttagggtt aatggttttt    2880
atagactaat ttttttagta catctatttt attctatttt agcctctaaa ttaagaaaac    2940
taaaactcta ttttagtttt tttatttaat aatttagata taaaatagaa taaaataaag    3000
tgactaaaaa ttaaacaaat acccttaag aaattaaaaa aactaaggaa acatttttct     3060
tgtttcgagt agataatgcc agcctgttaa acgccgtcga cgagtctaac ggacaccaac    3120
cagcgaacca gcagcgtcgc gtcgggccaa gcgaagcaga cggcacggca tctctgtcgc    3180
tgcctctgga cccctctcga gagttccgct ccaccgttgg acttgctccg ctgtcggcat    3240
ccagaaattg cgtggcggag cggcagacgt gagccggcac ggcaggcggc ctcctcctcc    3300
tctcacggca ccggcagcta cggggattc cttcccacc gctccttcgc tttcccttcc     3360
tcgcccgccg taataaatag acaccccctc cacaccctct ttccccaacc tcgtgttgtt    3420
cggagcgcac acacacacaa ccagatctcc cccaaatcca cccgtcggca cctccgcttc    3480
```

```
aaggtacgcc gctcgtcctc cccccccccc cctctctacc ttctctagat cggcgttccg    3540
gtccatggtt agggcccggt agttctactt ctgttcatgt ttgtgttaga tccgtgtttg    3600
tgttagatcc gtgctgctag cgttcgtaca cggatgcgac ctgtacgtca gacacgttct    3660
gattgctaac ttgccagtgt ttctctttgg ggaatcctgg gatggctcta gccgttccgc    3720
agacgggatc gatttcatga ttttttttgt ttcgttgcat agggtttggt ttgcccttt     3780 cctttatttc aatatatgcc gtgcacttgt ttgtcgggtc atcttttcat gcttttttt     3840 gtcttggttg tgatgatgtg gtctggttgg gcggtcgttc tagatcggag tagaattctg    3900
tttcaaacta cctggtggat ttattaattt tggatctgta tgtgtgtgcc atacatattc    3960
atagttacga attgaagatg atggatggaa atatcgatct aggataggta tacatgttga    4020
tgcgggtttt actgatgcat atacagagat gcttttgtt cgcttggttg tgatgatgtg     4080
gtgtggttgg gcggtcgttc attcgttcta gatcggagta gaatactgtt tcaaactacc    4140
tggtgtattt attaatttg gaactgtatg tgtgtgtcat acatcttcat agttacgagt     4200
ttaagatgga tggaaatatc gatctaggat aggtatacat gttgatgtgg ttttactga    4260 tgcatataca tgatggcata tgcagcatct attcatatgc tctaaccttg agtacctatc    4320
tattataata aacaagtatg ttttataatt attttgatct tgatatactt ggatgatggc    4380
atatgcagca gctatatgtg gatttttta gccctgcctt catacgctat ttatttgctt     4440
ggtactgttt cttttgtcga tgctcaccct gttgtttggt gttacttctg cagggatccc    4500
cgatcatgca aaaactcatt aactcagtgc aaaactatgc ctgggcagc aaaacggcgt     4560 tgactgaact ttatggtatg gaaaatccgt ccagccagcc gatggccgag ctgtggatgg    4620
gcgcacatcc gaaaagcagt tcacgagtgc agaatgccgc cggagatatc gtttcactgc    4680
gtgatgtgat tgagagtgat aaatcgactc tgctcggaga ggccgttgcc aaacgctttg    4740
gcgaactgcc tttcctgttc aaagtattat gcgcagcaca gccactctcc attcaggttc    4800
atccaaacaa acacaattct gaaatcggtt ttgccaaaga aaatgccgca ggtatcccga    4860
tggatgccgc cgagcgtaac tataaagatc ctaaccacaa gccggagctg ttttttgcgc    4920
tgacgccttt ccttgcgatg aacgcgtttc gtgaattttc cgagattgtc tccctactcc    4980
agccggtcgc aggtgcacat ccggcgattg ctcactttt acaacagcct gatgccgaac     5040
gtttaagcga actgttcgcc agcctgttga atatgcaggg tgaagaaaaa tcccgcgcgc    5100
tggcgatttt aaaatcggcc ctcgatagcc agcagggtga accgtggcaa acgattcgtt    5160
taatttctga attttacccg gaagacagcg gtctgttctc cccgctattg ctgaatgtgg    5220
tgaaattgaa ccctggcgaa gcgatgttcc tgttcgctga acaccgcac gcttacctgc     5280 aaggcgtggc gctggaagtg atggcaaact ccgataacgt gctgcgtgcg ggtctgacgc    5340
ctaaatacat tgatattccg gaactggttg ccaatgtgaa attcgaagcc aaaccggcta    5400
accagttgtt gacccagccg gtgaaacaag gtgcagaact ggacttcccg attccagtgg    5460
atgattttgc cttctcgctg catgaccta gtgataaaga aaccaccatt agccagcaga    5520
gtgccgccat tttgttctgc gtcgaaggcg atgcaacgtt gtggaaaggt tctcagcagt    5580
tacagcttaa accgggtgaa tcagcgttta ttgccgccaa cgaatcaccg gtgactgtca    5640
aaggccacgg ccgtttagcg cgtgtttaca acaagctgta agagcttact gaaaaaatta    5700
acatctcttg ctaagctggg agctcgatcc gtcgacctgc agatcgttca aacatttggc    5760
aataaagttt cttaagattg aatcctgttg ccggtcttgc gatgattatc atataatttc    5820
tgttgaatta cgttaagcat gtaataatta acatgtaatg catgacgtta tttatgagat    5880
```

-continued

```
gggttttat gattagagtc ccgcaattat acatttaata cgcgatagaa aacaaaatat    5940
agcgcgcaaa ctaggataaa ttatcgcgcg cggtgtcatc tatgttacta gatctgctag    6000
ccctgcagga aatttaccgg tgcccgggcg ccagcatgg ccgtatccgc aatgtgttat     6060
taagttgtct aagcgtcaat ttgtttacac cacaatatat                          6100
```

<210> SEQ ID NO 38
<211> LENGTH: 6
<212> TYPE: PRT
<213> ORGANISM: Zea mays

<400> SEQUENCE: 38

Ser Glu Lys Asp Glu Leu
1               5

<210> SEQ ID NO 39
<211> LENGTH: 20
<212> TYPE: DNA
<213> ORGANISM: Artificial Sequence
<220> FEATURE:
<223> OTHER INFORMATION: AmyF1n-5' primer

<400> SEQUENCE: 39

```
ccatgcaaat gcaagtcgta                                                  20
```

<210> SEQ ID NO 40
<211> LENGTH: 27
<212> TYPE: DNA
<213> ORGANISM: Artificial Sequence
<220> FEATURE:
<223> OTHER INFORMATION: AmyF1n-3' primer

<400> SEQUENCE: 40

```
aaagggtatt tgtttaattt ttagtca                                          27
```

<210> SEQ ID NO 41
<211> LENGTH: 19
<212> TYPE: DNA
<213> ORGANISM: Artificial Sequence
<220> FEATURE:
<223> OTHER INFORMATION: AmyF2-5' primer

<400> SEQUENCE: 41

```
aatccagggg taccagctt                                                   19
```

<210> SEQ ID NO 42
<211> LENGTH: 20
<212> TYPE: DNA
<213> ORGANISM: Artificial Sequence
<220> FEATURE:
<223> OTHER INFORMATION: AmyF2-3' primer

<400> SEQUENCE: 42

```
gctcaaaagt cagcctgtca                                                  20
```

<210> SEQ ID NO 43
<211> LENGTH: 3304
<212> TYPE: DNA
<213> ORGANISM: Zea mays

<400> SEQUENCE: 43

```
ccatgcaaat gcaagtcgta cgtctctctt tccagaattc agcagcagta ctctccacgc     60
actgatcgcc gtcagagagc taggtcagtg gctgcagtga gtgggcatga tgagtgcgtg    120
atgagggctc ttttggagct actactacta gcgtgtgtat tcattcactc tcactggccg    180
```

-continued

```
ataaactgac catctattta tctccaatcg atcgaattca tcagaccaga ttctctttta    240
tggccggccg gccggccctg ctgactgctg acgcggccaa acactgatag tttaaactga    300
aggcgggaaa cgacaatctg atcatgagcg gagaattaag ggagtcacgt tatgaccccc    360
gccgatgacg cgggacaagc cgttttacgt ttggaactga cagaaccgca acgctgcagg    420
aattggccgc agcggccatt taaatcaatt gggcgcgccg aattcgagct cggtacaagc    480
ttcgatcatc caggtgcaac cgtataagtc ctaaagtggt gaggaacacg aaacaaccat    540
gcattggcat gtaaagctcc aagaatttgt tgtatcctta acaactcaca gaacatcaac    600
caaaattgca cgtcaagggt attgggtaag aaacaatcaa acaaatcctc tctgtgtgca    660
aagaaacacg gtgagtcatg ccgagatcat actcatctga tatacatgct tacagctcac    720
aagacattac aaacaactca tattgcatta caaagatcgt ttcatgaaaa ataaaatagg    780
ccggacagga caaaaatcct tgacgtgtaa agtaaattta caacaaaaaa aaagccatat    840
gtcaagctaa atctaattcg ttttacgtag atcaacaacc tgtagaaggc aacaaaactg    900
agccacgcag aagtacagaa tgattccaga tgaaccatcg acgtgctacg taaagagagt    960
gacgagtcat atacatttgg caagaaacca tgaagctgcc tacagccgtc tcggtggcat   1020
aagaacacaa gaaattgtgt taattaatca aagctataaa taacgctcgc atgcctgtgc   1080
acttctccat caccaccact gggtcttcag accattagct ttatctactc cagagcgcag   1140
aagaacccga tcgacaggat ccaccatgag ggtgttgctc gttgccctcg ctctcctggc   1200
tctcgctgcg agcgccacca gcgctaagta cctggagctg gaggagggcg gcgtgatcat   1260
gcaggcgttc tactgggacg tcccgagcgg aggcatctgg tgggacacca tccgccagaa   1320
gatccccgag tggtacgacg ccggcatctc cgcgatctgg ataccgccag cttccaaggg   1380
catgtccggg ggctactcga tgggctacga cccgtacgac tacttcgacc tcggcgagta   1440
ctaccagaag ggcacggtgg agacgcgctt cgggtccaag caggagctca tcaacatgat   1500
caacacggcg cacgcctacg gcatcaaggt catcgcggac atcgtgatca accacagggc   1560
cggcggcgac ctggagtgga acccgttcgt cggcgactac acctggacgg acttctccaa   1620
ggtcgcctcc ggcaagtaca ccgccaacta cctcgacttc caccccaacg agctgcacgc   1680
gggcgactcc ggcacgttcg gcggctaccc ggacatctgc cacgacaagt cctgggacca   1740
gtactggctc tgggcctcgc aggagtccta cgcggcctac ctgcgctcca tcggcatcga   1800
cgcgtggcgc ttcgactacg tcaagggcta cggggcctgg gtggtcaagg actggctcaa   1860
ctggtggggc ggctgggcgg tgggcgagta ctgggacacc aacgtcgacg cgctgctcaa   1920
ctgggcctac tcctccggcg ccaaggtgtt cgacttcccc ctgtactaca agatggacgc   1980
ggccttcgac aacaagaaca tcccggcgct cgtcgaggcc ctgaagaacg gcggcacggt   2040
ggtctcccgc gacccgttca aggccgtgac cttcgtcgcc aaccacgaca cggacatcat   2100
ctggaacaag tacccggcgt acgccttcat cctcacctac gagggccagc ccacgatctt   2160
ctaccgcgac tacgaggagt ggctgaacaa ggacaagctc aagaacctga tctggattca   2220
cgacaacctc gcgggcggct ccactagtat cgtgtactac gactccgacg agatgatctt   2280
cgtccgcaac ggctacggct ccaagcccgg cctgatcacg tacatcaacc tgggctcctc   2340
caaggtgggc cgctgggtgt acgtcccgaa gttcgccggc gcgtgcatcc acgagtacac   2400
cggcaacctc ggcggctggg tggacaagta cgtgtactcc tccggctggg tctacctgga   2460
ggccccggcc tacgaccccg ccaacggcca gtacggctac tccgtgtggt cctactgcgg   2520
cgtcggctcc gagaaggacg agctgtgata ggtaacgaaa ctagagctct agatctgttc   2580
```

```
tgcacaaagt ggagtagtca gtcatcgatc aggaaccaga caccagactt ttattcatac    2640
agtgaagtga agtgaagtgc agtgcagtga gttgctggtt tttgtacaac ttagtatgta    2700
tttgtatttg taaaatactt ctatcaataa aatttctaat tcctaaaacc aaaatccagg    2760
ggtaccagct tgcatgcctg cagtgcagcg tgacccggtc gtgcccctct ctagagataa    2820
tgagcattgc atgtctaagt tataaaaaat taccacatat ttttttttgtc acacttgttt    2880 gaagtgcagt ttatctatct ttatacatat atttaaactt tactctacga ataatataat    2940
ctatagtact acaataatat cagtgtttta gagaatcata taaatgaaca gttagacatg    3000
gtctaaagga caattgagta ttttgacaac aggactctac agttttatct ttttagtgtg    3060
catgtgttct cctttttttt tgcaaatagc ttcacctata taatacttca tccatttat     3120 tagtacatcc atttagggtt tagggttaat ggtttttata gactaatttt tttagtacat    3180
ctattttatt ctattttagc ctctaaatta agaaaactaa aactctattt tagttttttt    3240
atttaataat ttagatataa aatagaataa aataaagtga ctaaaaatta aacaaatacc    3300
cttt                                                                 3304

<210> SEQ ID NO 44
<211> LENGTH: 3943
<212> TYPE: DNA
<213> ORGANISM: Zea mays

<400> SEQUENCE: 44
aatccagggg taccagcttg catgcctgca gtgcagcgtg acccggtcgt gcccctctct      60
agagataatg agcattgcat gtctaagtta taaaaaatta ccacatattt ttttttgtcac    120 acttgtttga agtgcagttt atctatcttt atacatatat ttaaacttta ctctacgaat    180
aatataatct atagtactac aataatatca gtgttttaga gaatcatata aatgaacagt    240
tagacatggt ctaaaggaca attgagtatt ttgacaacag gactctacag ttttatcttt    300
ttagtgtgca tgtgttctcc tttttttttg caaatagctt cacctatata tacttcatc    360 catttttatta gtacatccat ttagggttta gggttaatgg tttttataga ctaatttttt   420
tagtacatct attttattct attttagcct ctaaattaag aaaactaaaa ctctatttta   480 gttttttttat ttaataattt agatataaaa tagaataaaa taaagtgact aaaaattaaa   540
caaataccct ttaagaaatt aaaaaaacta aggaaacatt tttcttgttt cgagtagata   600
atgccagcct gttaaacgcc gtcgacgagt ctaacggaca ccaaccagcg aaccagcagc   660
gtcgcgtcgg gccaagcgaa gcagacggca cggcatctct gtcgctgcct ctggacccct   720
ctcgagagtt ccgctccacc gttggacttg ctccgctgtc ggcatccaga aattgcgtgg   780
cggagcggca gacgtgagcc ggcacggcag gcggcctcct cctcctctca ggcaccggc    840 agctacgggg gattcctttc ccaccgctcc ttcgctttcc cttcctcgcc cgccgtaata    900
aatagacacc cctccacac cctctttccc caacctcgtg ttgttcggag cgcacacaca    960
cacaaccaga tctcccccaa atccacccgt cggcacctcc gcttcaaggt acgccgctcg   1020
tcctcccccc ccccccctct ctaccttctc tagatcggcg ttccggtcca tggttagggc    1080
ccggtagttc tacttctgtt catgtttgtg ttagatccgt gtttgtgtta gatccgtgct    1140
gctagcgttc gtacacggat gcgacctgta cgtcagacac gttctgattg ctaacttgcc    1200
agtgtttctc tttggggaat cctgggatgg ctctagccgt tccgcagacg ggatcgattt    1260
catgattttt tttgtttcgt tgcatagggt ttggtttgcc cttttccttt atttcaatat    1320
atgccgtgca cttgtttgtc gggtcatctt ttcatgcttt ttttttgtctt ggttgtgatg   1380
```

| | | | | | |
|---|---|---|---|---|---|
| atgtggtctg | gttgggcggt | cgttctagat | cggagtagaa | ttctgtttca | aactacctgg | 1440 |
| tggatttatt | aattttggat | ctgtatgtgt | gtgccataca | tattcatagt | tacgaattga | 1500 |
| agatgatgga | tggaaatatc | gatctaggat | aggtatacat | gttgatgcgg | gttttactga | 1560 |
| tgcatataca | gagatgcttt | ttgttcgctt | ggttgtgatg | atgtggtgtg | gttgggcggt | 1620 |
| cgttcattcg | ttctagatcg | gagtagaata | ctgtttcaaa | ctacctggtg | tatttattaa | 1680 |
| ttttggaact | gtatgtgtgt | gtcatacatc | ttcatagtta | cgagtttaag | atggatggaa | 1740 |
| atatcgatct | aggataggta | tacatgttga | tgtgggtttt | actgatgcat | atacatgatg | 1800 |
| gcatatgcag | catctattca | tatgctctaa | ccttgagtac | ctatctatta | taataaacaa | 1860 |
| gtatgtttta | taattatttt | gatcttgata | tacttggatg | atggcatatg | cagcagctat | 1920 |
| atgtggattt | tttagccct | gccttcatac | gctatttatt | tgcttggtac | tgtttctttt | 1980 |
| gtcgatgctc | accctgttgt | ttggtgttac | ttctgcaggg | atccccgatc | atgcaaaaac | 2040 |
| tcattaactc | agtgcaaaac | tatgcctggg | gcagcaaaac | ggcgttgact | gaactttatg | 2100 |
| gtatggaaaa | tccgtccagc | cagccgatgg | ccgagctgtg | gatgggcgca | catccgaaaa | 2160 |
| gcagttcacg | agtgcagaat | gccgccgag | atatcgtttc | actgcgtgat | gtgattgaga | 2220 |
| gtgataaatc | gactctgctc | ggagaggccg | ttgccaaacg | ctttggcgaa | ctgcctttcc | 2280 |
| tgttcaaagt | attatgcgca | gcacagccac | tctccattca | ggttcatcca | aacaaacaca | 2340 |
| attctgaaat | cggttttgcc | aaagaaaatg | ccgcaggtat | cccgatggat | gccgccgagc | 2400 |
| gtaactataa | agatcctaac | cacaagccgg | agctggtttt | tgcgctgacg | cctttccttg | 2460 |
| cgatgaacgc | gtttcgtgaa | ttttccgaga | ttgtctccct | actccagccg | gtcgcaggtg | 2520 |
| cacatccggc | gattgctcac | tttttacaac | agcctgatgc | cgaacgttta | agcgaactgt | 2580 |
| tcgccagcct | gttgaatatg | cagggtgaag | aaaaatcccg | cgcgctggcg | attttaaaat | 2640 |
| cggccctcga | tagccagcag | ggtgaaccgt | ggcaaacgat | tcgtttaatt | tctgaatttt | 2700 |
| acccggaaga | cagcggtctg | ttctccccgc | tattgctgaa | tgtggtgaaa | ttgaaccctg | 2760 |
| gcgaagcgat | gttcctgttc | gctgaaacac | cgcacgctta | cctgcaaggc | gtggcgctgg | 2820 |
| aagtgatggc | aaactccgat | aacgtgctgc | gtgcgggtct | gacgcctaaa | tacattgata | 2880 |
| ttccggaact | ggttgccaat | gtgaaattcg | aagccaaacc | ggctaaccag | ttgttgaccc | 2940 |
| agccggtgaa | acaaggtgca | gaactggact | tcccgattcc | agtggatgat | tttgccttct | 3000 |
| cgctgcatga | ccttagtgat | aaagaaacca | ccattagcca | gcagagtgcc | gccattttgt | 3060 |
| tctgcgtcga | aggcgatgca | acgttgtgga | aaggttctca | gcagttacag | cttaaaccgg | 3120 |
| gtgaatcagc | gtttattgcc | gccaacgaat | caccggtgac | tgtcaaaggc | cacggccgtt | 3180 |
| tagcgcgtgt | ttacaacaag | ctgtaagagc | ttactgaaaa | aattaacatc | tcttgctaag | 3240 |
| ctgggagctc | gatccgtcga | cctgcagatc | gttcaaacat | ttggcaataa | agtttcttaa | 3300 |
| gattgaatcc | tgttgccggt | cttgcgatga | ttatcatata | atttctgttg | aattacgtta | 3360 |
| agcatgtaat | aattaacatg | taatgcatga | cgttatttat | gagatgggtt | tttatgatta | 3420 |
| gagtcccgca | attatacatt | taatacgcga | tagaaaacaa | aatatagcgc | gcaaactagg | 3480 |
| ataaattatc | gcgcgcggtg | tcatctatgt | tactagatct | gctagccctg | caggaaattt | 3540 |
| accggtgccc | gggcggccag | catggccgta | tccgcaatgt | gttattaagt | tgtctaagcg | 3600 |
| tcaatttgtt | tacaccacaa | tatattcaag | tcatctgcat | gtgaaataaa | catcttgtcc | 3660 |
| ctcctcgatg | atccacctct | ctctctctct | ctctctctct | ctctctctct | ctctctctct | 3720 |
| ctcatgctca | attgctcatg | catatgcacg | cgcgcgtttg | ctcgcccatt | gtttgtttgc | 3780 |

```
ttttgctttt atgttcgatc gatggatgta tgtgtatata ggcgagaagg ggcaccagct    3840
gctgcatgcc tgtttcttac agtcttgtat tgtatgcatg caaaagagag aagctagact    3900
agaccagaca acactagcga ttctgacagg ctgacttttg agc                      3943
```

<210> SEQ ID NO 45
<211> LENGTH: 26
<212> TYPE: DNA
<213> ORGANISM: Artificial Sequence
<220> FEATURE:
<223> OTHER INFORMATION: Es3272-5' Forward Primer

<400> SEQUENCE: 45

```
tcatcagacc agattctctt ttatgg                                           26
```

<210> SEQ ID NO 46
<211> LENGTH: 20
<212> TYPE: DNA
<213> ORGANISM: Artificial Sequence
<220> FEATURE:
<223> OTHER INFORMATION: Es3272-5' Reverse Primer

<400> SEQUENCE: 46

```
cgtttcccgc cttcagttta                                                  20
```

<210> SEQ ID NO 47
<211> LENGTH: 23
<212> TYPE: DNA
<213> ORGANISM: Artificial Sequence
<220> FEATURE:
<223> OTHER INFORMATION: Es3272-5' Probe

<400> SEQUENCE: 47

```
actgctgacg cggccaaaca ctg                                              23
```

<210> SEQ ID NO 48
<211> LENGTH: 27
<212> TYPE: DNA
<213> ORGANISM: Artificial Sequence
<220> FEATURE:
<223> OTHER INFORMATION: ESPCR0026 Primer

<400> SEQUENCE: 48

```
catgatgagt gcgtgatgag ggctctt                                          27
```

<210> SEQ ID NO 49
<211> LENGTH: 28
<212> TYPE: DNA
<213> ORGANISM: Artificial Sequence
<220> FEATURE:
<223> OTHER INFORMATION: ESPCR0004 Reverse Primer

<400> SEQUENCE: 49

```
gtatgatctc ggcatgactc accgtgtt                                         28
```

<210> SEQ ID NO 50
<211> LENGTH: 23
<212> TYPE: DNA
<213> ORGANISM: Artificial Sequence
<220> FEATURE:
<223> OTHER INFORMATION: Zm Adh1 Forward Primer

<400> SEQUENCE: 50

```
cgtcgtttcc catctcttcc tcc                                              23
```

```
<210> SEQ ID NO 51
<211> LENGTH: 20
<212> TYPE: DNA
<213> ORGANISM: Artificial Sequence
<220> FEATURE:
<223> OTHER INFORMATION: Zm Adh1 Reverse Primer

<400> SEQUENCE: 51
ccactccgag accctcagtc                                               20

<210> SEQ ID NO 52
<211> LENGTH: 27
<212> TYPE: DNA
<213> ORGANISM: Artificial Sequence
<220> FEATURE:
<223> OTHER INFORMATION: Zm Adh1 Probe

<400> SEQUENCE: 52
aatcagggct cattttctcg ctcctca                                       27
```